United States Patent
Lakritz et al.

(10) Patent No.: US 9,406,052 B2
(45) Date of Patent: Aug. 2, 2016

(54) RESOURCE SCHEDULING AND MONITORING

(71) Applicants: Kenneth B. Lakritz, Winchester, MA (US); Michael J. Frankston, Lincoln, MA (US)

(72) Inventors: Kenneth B. Lakritz, Winchester, MA (US); Michael J. Frankston, Lincoln, MA (US)

(*) Notice: Subject to any disclaimer, the term of this patent is extended or adjusted under 35 U.S.C. 154(b) by 0 days.

(21) Appl. No.: 14/494,009

(22) Filed: Sep. 23, 2014

(65) Prior Publication Data
US 2015/0142493 A1    May 21, 2015

Related U.S. Application Data

(63) Continuation of application No. 12/464,536, filed on May 12, 2009, now Pat. No. 8,874,456, which is a continuation of application No. 10/974,005, filed on Oct. 25, 2004, now abandoned.

(60) Provisional application No. 60/513,666, filed on Oct. 23, 2003.

(51) Int. Cl.
| | |
|---|---|
| *G06F 9/46* | (2006.01) |
| *G06Q 10/10* | (2012.01) |
| *G06F 9/48* | (2006.01) |
| *G06Q 10/06* | (2012.01) |
| *G06F 19/00* | (2011.01) |
| *H04L 12/24* | (2006.01) |

(52) U.S. Cl.
CPC .............. *G06Q 10/1093* (2013.01); *G06F 9/46* (2013.01); *G06F 9/4881* (2013.01); *G06Q 10/06* (2013.01); *G06Q 10/06312* (2013.01); *G06Q 10/06314* (2013.01); *G06Q 10/06315* (2013.01); *G06F 19/322* (2013.01); *H04L 12/24* (2013.01)

(58) Field of Classification Search
None
See application file for complete search history.

(56) References Cited

U.S. PATENT DOCUMENTS

| | | | | |
|---|---|---|---|---|
| 5,111,391 | A | * | 5/1992 | Fields et al. ................ 705/7.14 |
| 5,343,388 | A | | 8/1994 | Wedelin |
| 5,406,476 | A | * | 4/1995 | Deziel et al. ................ 705/7.15 |

(Continued)

FOREIGN PATENT DOCUMENTS

CA        2063974        9/1992

OTHER PUBLICATIONS

Acuna, S.T., et al., "The Software Process: Modelling, Evaluation and Improvement", In *Handbook of Software Engineering and Knowledge Engineering*, (World Scientific Publishing Company, 0(0): 1-35 (2000).

(Continued)

*Primary Examiner* — Gurkanwaljit Singh
(74) *Attorney, Agent, or Firm* — Hamilton, Brook, Smith & Reynolds, P.C.

(57) ABSTRACT

A resource scheduling system includes a set of resources and associated resource attributes, a representation of resource demands, and a scheduling module for generating a schedule of resource utilization. The representation of resource demands and availability may include information about time slots, calendars, and shifts. A slot is a representation of a demand for one or more individual item. A calendar is a representation of dates when resources are needed. Each shift represents a set of time intervals of resource demands. Additionally, the system keeps track of individual resource availability and preferences and attempts to create a resource utilization schedule that satisfies all constraints generated based on the time slots, calendars, shifts, and resource schedules.

32 Claims, 5 Drawing Sheets

(56) References Cited

U.S. PATENT DOCUMENTS

| | | | |
|---|---|---|---|
| 5,408,663 A * | 4/1995 | Miller | 718/104 |
| 5,467,268 A * | 11/1995 | Sisley et al. | 705/7.16 |
| 5,794,172 A | 8/1998 | Matheson et al. | |
| 5,842,173 A * | 11/1998 | Strum et al. | 705/2 |
| 6,003,061 A * | 12/1999 | Jones et al. | 718/104 |
| 6,049,776 A * | 4/2000 | Donnelly et al. | 705/7.14 |
| 6,216,109 B1 * | 4/2001 | Zweben et al. | 705/7.12 |
| 6,341,303 B1 * | 1/2002 | Rhee et al. | 718/104 |
| 6,571,215 B1 * | 5/2003 | Mahapatro | 705/7.12 |
| 6,823,315 B1 * | 11/2004 | Bucci et al. | 705/7.16 |
| 6,850,895 B2 * | 2/2005 | Brodersen et al. | 705/7.14 |
| 8,306,841 B2 * | 11/2012 | Clarke | 705/7.23 |
| 8,315,901 B2 * | 11/2012 | Cameron et al. | 705/7.13 |
| 8,448,015 B2 * | 5/2013 | Gerhart | 714/4.4 |
| 8,874,456 B2 | 10/2014 | Lakritz et al. | |
| 2001/0051888 A1 * | 12/2001 | Mayhak et al. | 705/8 |
| 2002/0029161 A1 * | 3/2002 | Brodersen et al. | 705/9 |
| 2003/0033180 A1 * | 2/2003 | Shekar et al. | 705/7 |
| 2003/0101091 A1 * | 5/2003 | Levin et al. | 705/11 |
| 2003/0208392 A1 * | 11/2003 | Shekar et al. | 705/8 |
| 2004/0039628 A1 * | 2/2004 | Thompson et al. | 705/9 |
| 2004/0158568 A1 * | 8/2004 | Colle et al. | 707/100 |
| 2004/0267595 A1 * | 12/2004 | Woodings et al. | 705/9 |
| 2006/0053043 A1 * | 3/2006 | Clarke | 705/8 |
| 2006/0167733 A1 * | 7/2006 | Scott et al. | 705/8 |
| 2006/0236368 A1 * | 10/2006 | Raja et al. | 726/1 |
| 2007/0083868 A1 * | 4/2007 | Sankaranarayan et al. | 718/104 |
| 2008/0027783 A1 * | 1/2008 | Hughes et al. | 705/9 |
| 2008/0172282 A1 * | 7/2008 | McNeill et al. | 705/9 |
| 2008/0270179 A1 * | 10/2008 | Meiner et al. | 705/2 |
| 2008/0300954 A1 * | 12/2008 | Cameron et al. | 705/9 |
| 2009/0006160 A1 * | 1/2009 | Boegner | 705/8 |
| 2009/0138322 A1 * | 5/2009 | Joyner et al. | 705/9 |
| 2009/0265205 A1 * | 10/2009 | Stinchcombe et al. | 705/8 |
| 2009/0299803 A1 | 12/2009 | Lakritz et al. | |

OTHER PUBLICATIONS

Apt., "Principles of Constraint Programming," *Cambridge University Press* (2003).

Baptiste, et al., "Constraint-Based Scheduling: Applying Constraint Programming to Scheduling Problems," *Kluwer Academic Publishers Group*, (2001).

Beaulieu, et al., "A Mathematical Programming Approach for Scheduling Physicians in the Emergency Room," *Health Care Management Science*, 3:193-200 (Feb. 4, 2000).

Blanton, K., "The Two Sides of Office Software: Working and Shirking," *The Boston Globe*, pp. C1, C5 (Sep. 15, 2003).

Carter, et al., "Scheduling Emergency Room Physicians," *Health Care Management Science*, 4:347-360 (Apr. 18, 2001).

Fowler, P. and Rifkin S., "Software Engineering Process Group Guide", Software Engineering Institute, Technical Report: CMU/SEI-90-TR-24, ESD-90-TR-225, pp. 1-159 (Sep. 1990).

"Global Knowledge Network to Provide Deutsche Telekom Customers and Employees with Competency-based SAP Training," PR Newswire (Nov. 24, 1998).

Nuitjen, W., "Constraint-Base Job Shop Scheduling with ILOG Scheduluer, *Journal of Heuristics*, 3: 271-286 (1998).

Sabin, et al., "Greater Efficiency for Conditional Constraint Satisfaction," *LNCS*, 2833:649-663 (2003).

Zweben, M. et al., "Learning to Improve Constraint-Based Scheduling", *Artificial Intelligence*, 58: 271-296 (1992).

Zweben, M. et al., "Scheduling and reschedule with iterative repair", Systems, Man and Cybernetics, IEEE Transactions on 23.6: 1588-1596 (1993).

Expressions and Operators (Java in a Nutshell), docstore.mik.ua/orelly/java-ent/jnut/ch02-05.htm, Apr. 2, 2002; p. 7.

* cited by examiner

RESOURCE SCHEDULING AND MONITORING

RELATED APPLICATIONS

This application is a continuation of Ser. No. 12/464,536 filed May 12, 2009 which is a continuation of U.S. application Ser. No. 10/974,005, filed Oct. 25, 2004, which claims the benefit of U.S. Provisional Application No. 60/513,666, filed on Oct. 23, 2003. The entire teachings of the above applications are incorporated herein by reference.

BACKGROUND OF THE INVENTION

To function effectively, complex organizations must coordinate the work schedules of many individual employees, different kinds of employees, and other resources. Moreover, because skilled and experienced workers are often a scarce resource, and because payroll is the single largest expense for many businesses, schedules must use employees' time as efficiently as possible. The preferences of individual employees as well as union and government regulations further constrain acceptable work patterns. Creating a work schedule that satisfies requirements like these—arising from multiple, potentially conflicting sources—is a challenging mathematical problem. In practice, it is often impossible to find the best schedule with 'pencil and paper' methods, even when a relatively small number of employees are involved.

As an example, consider the problem of staffing a hospital ward, an emergency room, or an operating room. An adequate staffing pattern must satisfy many requirements: a certain number of doctors must always be physically present, another number of doctors must be available 'on call,' and these numerical demands will be higher during hours and days of expected peak demand. Among the doctors present, several must be senior or board-certified physicians. Physicians in training cannot legally work more than 100 hours per week, or more than 36 hours consecutively. Operating room teams must be scheduled together, and must be present whenever a surgeon is present. There must be at least one physician anesthesiologist to supervise every three nurse anesthetists. Staff with various religious affiliations will be unavailable on certain days of the week and on religious holidays that vary from one religion to another. Other employees may be unwilling or unable to work night shifts, or to work more than half time. Some employees may dislike each other and demand that their schedules not overlap. No one in the nurses' union can be required to work on three consecutive weekends, and no one can be in two places at once.

A traditional way to deal with such overwhelming complexity is simply to avoid it. Organizations routinely create work schedules by disregarding individual preferences and by fitting their workers into simple, fixed, repeating shifts. But overly rigid schedules are inefficient and waste employees' time. And when skilled workers are in demand, businesses are at a competitive disadvantage unless they can offer potential employees flexibility and consideration of their individual needs.

It is therefore desirable to have systems that automate the difficult process of constructing employee schedules. Many currently available employee scheduling systems are little more than 'fill-in' programs. They allow a user to enter an employee name into a work position on a single day or on a succession of days and then reformat the schedule and compile hourly work statistics. A few more sophisticated programs allow users to choose from a small number of hard-wired scheduling patterns or templates, and help the user fill those in.

SUMMARY OF THE INVENTION

The present invention relates to a computer method and system for calculating work schedules for employees in an organization and, more generally, for calculating the scheduled allocation of constrained resources. Because the system's constraint language for specifying problems and the automatic scheduling algorithm used to solve these problems are so flexible, they may be used to set up and solve many 'NP-Complete' problems. One aspect of the present invention is a highly flexible system and method for setting up a very broad variety of employee scheduling and other resource allocation problems subject to an unlimited number and kinds of constraints and automatically solving those problems. Having constructed an acceptable schedule, the system may also help employers track the actual attendance of employees. When employees are unexpectedly absent, the system may guide the employer in finding suitable available substitutes.

In one aspect of the invention, a resource scheduling system includes a set of resources and associated resource attributes, a representation of resource demands, and a scheduling module for generating a schedule of resource utilization. The representation of resource demands may include information about time slots. A slot is a representation of a demand for one or more individual items. The representation for resource demands may also include calendars, which represent dates for resource utilization. The system may automatically create calendars based on those already entered in the system. Additionally, resource demands may be expressed as one or more shifts, each shift representing a set of time intervals of resource demands.

A set of constraints may be generated either automatically by the system, or manually by a user, the set of constraints taking into account resource demands and resource availability information. Such resource availability information may include resource schedules, which denote when a particular resource is available for scheduling.

Resource constraints may be entered or edited by a system user using a graphic user interface that allows for easy constraint creation. In the user interface, constraints and/or their parts may be displayed using natural language, so that the user does not need to use a programming language to create or edit a particular constraint. In order to use the natural language for constraint creation, the user interface presents a range of choices for each of the constraint components and parts.

System user interface may also allow for creating, modifying and displaying descriptive attributes of resources and for creating an acceptable range of values of each such attribute, as well as for associating to each type of resource in the system, a subset of said descriptive attributes that describe objects of the type. The types of data objects may include individual resource items, calendar sets, shifts, slots, assignments, substitutions and absences. The user interface may also allow for assigning a name to every object, thereby preventing two objects of the same type from having identical names, and for assigning values to an object for any attribute associated with the type of a particular object. An object may be switched between active and inactive status. Additional classes of constraints that limit and describe acceptable schedules may be used.

The resource utilization system may then automatically construct resource schedules, each schedule representing an assignment of individual resource items to instances of demand for resources as denoted by a system of shifts and slots, subject to the limitations of resource availability, patterns of demand, and other constraints. Where no such schedule is possible, the system may generate and present diagnostic information, identifying resource shortages and irresolvable conflicts among the demands, resource availability and constraints.

Descriptive attributes may have names and data types. Every resource has a unique name and may also have other attributes. Each attribute must belong to one of several types. Each data type may be one or more of the following: an integer type, a numeric type, an enumerated type, a Boolean type, and a string type. Thus, acceptable values for attributes are restricted, attributes of integer type accepting integer values only, attributes of number type accepting values of positive or negative rational numbers only, attributes of enumerated type accepting as values only a finite set of alphanumeric strings, attributes of Boolean type accepting as values only 'true' or 'false', and attributes of string type accepting as values any alphanumeric string.

Resource constraints may be conditional, depending on a set of previously made assignments. In general, a constraint may be expressed as zero or more "if" clauses and one or more "then" clauses. During the scheduling, the system may generate a list of resource slots and then attempt to assign individual resources to those slots. If no assignment is possible, a partial schedule may be presented to a user. In addition, the system may generate diagnostic information, including indication of resource and utilization availability and/or constraint conflicts.

The system user interface may allow for manual modification of resource schedules, or for "accepting" a particular schedule and generating a permanent record of it. Furthermore, a user may activate or deactivate resources and/or constraints to test how those modifications will affect overall scheduling. In addition to scheduling resources, the system may keep track of resource utilization and of individual resource utilization. For example, numeric resource attributes may be declared cumulative, and the scheduling system may then sum up those attributes across an appropriate group of scheduled assignments. In this way, a user may be able to generate cost or other estimates.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The system and methods described herein can be used for solving general resource scheduling problems in a variety of environments. In the case of employee scheduling problems, employees are the resources, but the algorithm and system described here are highly general and can allocate or schedule many other kinds of resources. For example, in scheduling one or more hospital operating rooms, employees, surgical equipment, and operating rooms are all tightly constrained resources that need to be scheduled and coordinated. A typical constraint might be, "No heart surgeon is scheduled for a heart transplant 'shift' unless a suitable operating room, an anesthesiologist, and a cardiopulmonary bypass team work the same 'shift'".

Similarly, in a factory, skilled workers, pieces of machinery and sub-assemblies are resources to be scheduled for the purpose of assembling a prescribed number of cars or computers.

An example of a less obvious kind of problem that the system can solve is the need for colleges to match up classes and classrooms. In this case, the classrooms are the resource to be allocated and the classes (or courses) are demands on the resource.

Figure 1:
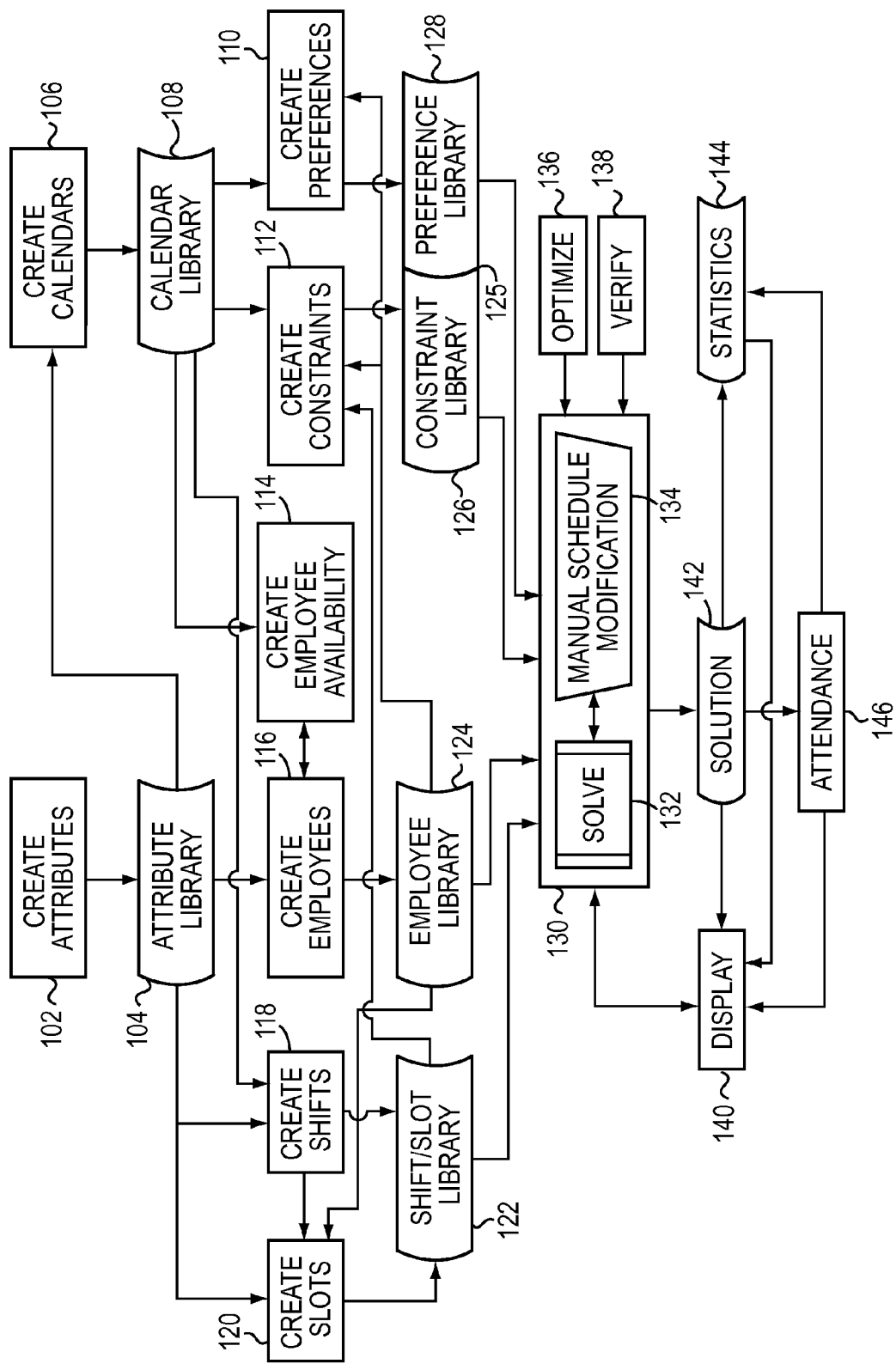
FIG. 1 is an illustration of the resource scheduling system according to one embodiment of the invention.

FIG. 1 is a flow chart of one embodiment of the invention as described below. In one embodiment of the system, the resources to be scheduled are individual employees of a business or other organization. To schedule his employees, an employer creates a database of the employees, assigning to each employee values of attributes relevant to scheduling, such as the employee's seniority, hourly pay or possession of needed skills. Each employee designates the days and times that he is available for work. The employer also creates a database of shifts, recurrent time periods during which a particular pattern of staffing is required, and associates with each shift one or more slots, each of which must be filled by one or more employees. The employer describes which employees may work in each slot by associating acceptable values of employee attributes with each slot. The employer may also create further constraints on the work schedule. These further constraints are in the form of maximal or minimal Time Limits, designating how much or how little time various classes of employees may work during specified time periods, or in the form of Conditional Constraints, describing patterns of work that must or must not occur. The employer may also require that the schedule minimize his payroll costs, or other measures. The employer or employees can also require that certain parts of the schedule be repetitive or 'regular', so that certain employees always work at the same time or in the same location. The system uses an algorithm to construct a schedule that meets all these requirements, if possible. If no such schedule exists because of irresolvable conflicts among the requirements, the algorithm helps the employer identify those conflicts, and offers suggestions for resolving them. When an acceptable schedule has been produced, it is printable in several formats, including formats suitable for distribution to individual employees. The system also records the actual attendance of employees, compares this with the calculated schedule, and helps the employer find substitute employees when scheduled employees are absent.

In one embodiment of the present invention, four semi-permanent data structures are created and maintained: employee library 124, shift or demand library 122, preference library 128, and constraint library 126. Two other libraries, attribute library 104 and calendar library 108, are used to help construct entries in the employee, shift, slot, and constraint libraries.

Depending upon the needs of the particular user, each of the libraries may be supplied to the user partially filled but allowing for user modification.

Each of the libraries may be in the form of a relational database and support all usual database functions. Each library entry has a unique numerical identifier. The user can also assign an optional alphanumeric name to any library entry. Libraries can be searched and ordered by identifier, by name, and by various properties or attributes of the entries.

Additionally, the following functions for managing the libraries are available:
1—Create a new entry
2—Delete an entry
3—Copy an entry
4—Modify an entry Scheduling problems are described by copying items from these libraries to create three more data structures—employee database 204 (FIG. 2), shift or demand database 206, and constraint database 208. Besides creating these three databases, the user sets the Start and End Dates of the time interval 210 to be scheduled. Intervals as brief as one day or as long as several years can be accommodated.

Attributes and Classes

In order to describe the details of a scheduling problem, the user may create any number of 'attributes' (Step 102) and place them in the attribute library 104. Attributes are descriptive properties of objects used in setting up a scheduling problem. Position, seniority, and specialty are examples of possible attributes of employees.

Each attribute is assigned one of five attribute types by the user. An attribute may be of Boolean, integer, numeric, enumerated, or string type. Boolean attributes take only the values 'yes' and 'no' or 'True' and 'False'. Integer attributes can take any whole number as a value, and the user may further designate maximal and/or minimal permissible values for an integer attribute. Numeric attributes can take any floating point number as a value and the user can designate maximal and/or minimal permissible values. For enumerated attributes, the user must supply a list of permissible values, each of which has the form of an alphanumeric character string. For string attributes any string of alphanumeric characters is a permissible value.

The user of the system can associate attributes with types of objects. There are seven of these types of objects: calendars, employees, shifts, slots, assignments, absences and replacements. Once an attribute is associated with a type of object, all objects of that type can be given values for that attribute.

Any attribute can also be declared 'private.' Private attributes express useful information about employees but are not displayed in the general employee library displays. Examples of common private attributes are employee's address, social security number or home telephone number.

Any integer or numerical attribute can also be declared 'cumulative.' Cumulative attributes support additional display and statistical procedures, involving the summation of the values of the attribute over a schedule. So, for example, 'Hourly Salary' is a useful cumulative attribute since summing it across a schedule will yield the payroll cost of the schedule, but 'height' and 'weight' of employees are usually not useful cumulative attributes.

Classes

Users can group objects into classes. Classes can be created either by listing their members or by specifying acceptable attribute values or ranges of values for membership in the class. The members of each class are limited to a single object type. Classes, once created, are named and stored in class libraries, where they can be modified and reused. Classes of the same type can be combined to form new classes, using Boolean operations: union, intersection, complementation and difference.

Calendars

The user can create and name any number of 'calendars' (step 106). A calendar is any collection of designated days. Some examples are the calendar of all Tuesdays, the calendar of all weekend days, and the calendar of all state holidays. Calendars for each weekday, and 'every day' are integral to the system and always available to the user. The system has facilities for displaying each calendar in the typical format of a wall calendar, with days in the calendar highlighted.

Individual days or blocks of days can be added to or removed from a calendar by highlighting and clicking on the appropriate entries. The system also permits existing calendars to be combined with one another using Boolean operations: union, intersection, complementation and difference. Once created and named, calendars are entered into calendar library 108 and are available for use throughout the system.

Every calendar has a name, an alphanumeric string, that uniquely identifies that calendar. The user may also associate any user-defined attribute with calendars.

Employees

The user can create and name any number of employees (step 116). Each employee has a name. When an employee or other resource is created, it is automatically assigned an internal system generated specifier. The user is prompted to enter the unique name that he wishes to use to identify the employee or resource. The name is an alphanumeric string, whose value uniquely identifies that employee or resource.

The user can associate any user-defined attribute with employees. Among employee attributes one is given special treatment—'Position.' Position is always an enumerated attribute, and is intended to provide an initial sorting of the employees into job categories. In a hospital staff scheduling problem, for example, the positions might be 'Doctor,' 'Nurse,' 'Administrator,' 'Technician', etc. Lists of positions appropriate to a wide range of work environments can also be supplied with the system or imported from other sources so that the user can find many, if not all, of the position titles he requires within existing lists.

The user may associate any other attribute either to all employees or just to those employees with a given position attribute value. So, for instance, doctors may have 'Specialty' and 'Board Certification' attributes but not an 'Hourly Salary' attribute, whereas nurses may have an 'Hourly Salary' attribute but not a 'Board Certification' attribute. Similarly, every employee may have an 'Age' and a 'Home Telephone Number' attribute.

The user enters employees into employee library 124, specifying for each employee the values of the relevant attributes. In each case, the entry of attribute values is set up so that values outside of any specified numerical limits, or values not on the enumerated list of acceptable values for an enumerated attribute, cannot be entered. The user may leave attribute fields blank. Lists of employees can also be brought in from other resource libraries and database systems.

The system allows each employee to specify what times he or she is available to work (step 114); the scheduling interval is broken down into segments, and an employee can designate that he is or is not available for each of those segments. The size of the segments is determined by the user. For instance, the segments can be made 15 minutes long each.

There are multiple ways for an employee to specify when he is available to work and he can combine these ways:

The employee can select a single time interval or a set of time intervals on a graphical representation of the scheduling interval and declare himself available or unavailable for the selected interval or intervals.

The employee can select a Calendar Class, a Shift Class and a Slot Class, and declare himself available or unavailable for every time interval occurring on a day in that Calendar Class and during which a shift within that Shift Class and containing a slot within that Slot Class occurs. So, for example, an employee can declare himself unavailable on Sundays, or for the 5 to 11 shift on weekends, or declare himself available to work whenever there is demand for a nurse in the emergency room.

Each time one of these operations is performed, the graphical representation of the employee's availability changes to reflect the change in his availability. The graphical representation of availability also displays a comparison between the employee's declared availability and those times during which the employee could potentially work, based on the employer's needs as expressed in the shift database.

There is an 'active/inactive' switch associated with each employee. When an employee is inactive, the system does not schedule him to work. Inactive employees are visible in the employee library but their names and attributes are displayed in gray rather than in black. The active/inactive switch allows the user to enter employee information once, save it in the employee library and have it available for future use. By using their ability to declare employees (and also shifts, slots and constraints) active or inactive, users can easily experiment with modifications in their scheduling problems. For instance, the user can explore the effect on payroll cost of adding or removing employees.

Besides displaying employees and their attributes in a database format, the system also allows the creation of a virtual 'index card' for each employee. The system contains a flexible form design feature for these cards, so that the employee and his attributes can appear in an unlimited range of formats. Each employee's index card also can display that employee's private attributes. Displays of the employee's availability, constraints, preferences and Time Limits relevant to that employee (these terms are explained below), the current schedule of that employee, the attendance history of that employee, and statistical reports on that employee's attendance and schedule can also be associated with the employee's index card.

Shifts

The user creates a demand or shift database 122 in step 118 to express the pattern of his needs for employees. This database is made up of any number of user-created shifts. Each shift expresses the request for a certain number and type of employee to work at specified and recurring times and days. The user can associate any number of user defined attributes with shifts. Each shift may have the following elements:

Name: The user may give each shift a name, so that it can be referred to in other parts of the system and in the system's outputs. The name is a unique alphanumeric character string specified by the user.

Start time: The user must specify the time of the day the shift begins.

End time: The user must specify the time of day the shift ends. (If the end time is earlier than the starting time, the shift is understood to extend from one day into the next.) Shifts can be up to 24 hours long.

Occurrence Calendars: The user must specify, by choosing one or more calendars from calendar library 108, all those days on which the shift occurs. If more than one calendar is chosen, the shift occurs on every day contained in at least one of the calendars chosen.

Rotation Calendar: The rotation calendar is a single calendar selected from the calendar library and specifies the size of the blocks into which the shift is broken for scheduling purposes. The default rotation calendar is 'Every Day,' causing the automatic scheduling algorithm to assign employees to the shift each day, independently of other days. In an alternative embodiment of the invention, a user may select different default calendars. If any other rotation calendar is chosen, the algorithm breaks up the scheduling interval for the shift into blocks running from one day of the rotation calendar up to, but not including, the next day of the rotation calendar, and assigns the same employees to the shift on every day within a block on which the shift occurs. For example, if the rotation calendar of a shift is 'Sunday,' employees are assigned to the shift, for each day the shift occurs, in one week rotations running from one Sunday to the next. Since the user can create additional calendars at will, he has complete control over the size and pattern of rotations. He can also use different rotation calendars for different shifts.

Slots: The user may associate any number of slots with a shift. Each of these associated slots represents a request for one or more employees to work during the shift. For example, a user could associate a slot for five nurses, a slot for two emergency specialist physicians and a slot for an on-call neurosurgeon with the morning emergency room shift. Each slot associated with a shift has an active/inactive switch. Inactive slots are shown in gray and are not filled by the automatic scheduling algorithm.

An 'Active/Inactive' switch (for the entire shift): Inactive shifts are shown in gray and none of their slots is filled by the automatic scheduling algorithm.

Slots

The user creates slot database 122 in step 120 to express patterns of demand for employees. This library is made up of any number of user-created slots. Each slot expresses a request for a certain number and type of employee to work. The user can associate any number of user defined attributes with slots. Each slot may have the following elements:

An (optional) name: An alphanumeric character string, which appears in the system's schedule outputs.

A Multiplicity: The multiplicity of a slot specifies the number of employees needed to fill the slot. The multiplicity is either an integer or a 'demand driven' function. The default value of the multiplicity of a slot is the integer 1. To create a demand function, the user first defines and enters values for any number of 'demand variables.' Demand variables are functions from dates to integers. For example, a car dealer might create a demand variable called 'Number of cars sold' to express a prediction of the number of cars he expects to sell on a given day based on past sales.

There are three ways to create demand variables:
1) They can be imported from demand variable libraries or from other programs,
2) Their values can be entered day by day, or
3) Their values can be entered graphically.

For any slot, the user may then define a 'slot demand function', by algebraically combining any number of demand variables. The value of the slot demand function corresponding to a slot on a given day defines the multiplicity or number of employees required to fill that slot on that day. If the rotation for a shift includes more than one day, the multiplicity for any slot in any day of the rotation is the maximum value of that slot's demand function calculated over all the days of the rotation.

For example, a car dealership could define a demand variable 'number of cars to be serviced' and then set the multiplicity of the 'mechanics' slot to be 1+(0.1 times the number of cars to be serviced).

A switch, 'Optional/Required': 'Required' slots must be filled whenever a schedule is constructed, and receive priority in the automatic scheduling process. Optional slots need not be filled in an acceptable schedule and the automatic scheduling algorithm fills optional slots as needed to satisfy scheduling constraints. The user may also direct the automatic scheduling algorithm to fill specified classes of optional slots where possible.

A means of designating the eligible employees for the slot: The user can designate the class of employees eligible to be assigned to a slot either by listing the eligible employees, selecting a previously defined class of employees or by designating the eligible employees by attribute value.

In designating the class of eligible employees by attribute value, the user can designate a range of acceptable values of that attribute for any number of employee attributes, including employee name. If acceptable values are designated for more than one attribute, eligible employees for the slot must have acceptable values for every designated attribute.

For example, if the attribute 'Position' is given the value range '=Surgeon', and the numerical attribute 'Seniority' is given the value range '>=15', only employees who are surgeons with 15 or more years 'Seniority' are eligible to fill the slot.

Values and Ranges

When the system requires the input of a value of an attribute, the user is prompted to enter either an integer, a floating point number, a character string, or to select from a list of choices, depending on whether the attribute is of integer, numerical, string, or enumerated type. If the attribute is of integer or numerical type and there are upper or lower limits defined for the attribute, these limits are also visible, and the user is prevented from entering values outside the limits.

At some points, the system requires input not of a single attribute value, but a range of acceptable attribute values. This occurs, for example, in the specification by attribute value of acceptable employees to fill a slot.

When the system requires the input of a range of values of a string or enumerated attribute, the user is prompted for an attribute value, as above, and also for a comparison operator. For string and enumerated attributes, the only comparison operators are 'equal to' and 'not equal to.'

When the system requires the input of a range of values for a numerical or integer attribute or other parameter, the above options are available.

Alternatively, the user may enter lower and upper bounds for the range and two comparison operators. Either bound may be omitted. Zero and 'unlimited' are the default values for the lower and upper bounds. The comparison operator for the lower bound is either 'greater than' or 'greater than or equal to' and the comparison operator for the upper bound is either 'less than' or 'less than or equal to.'

Constraints

The user can create any number of constraints (step 112) to further specify and restrict acceptable schedules. Constraints are archived in constraint library 126 so that, once created, they can be reused.

Each scheduling problem has associated with it a database of constraints. The user can add or delete constraints from this database. When the user attempts to associate a constraint with a scheduling problem the system checks that all the terms in the constraint are defined for that scheduling problem. Constraints in the database of a scheduling problem can be toggled between active and inactive states. Inactive constraints are ignored in the scheduling process.

As constraints are constructed, they are immediately translated into English language paraphrases that are visible to the user. Highlighting any part of such a paraphrase makes visible and available for modification the choices in the constraint entry screen that were used to generate that part of the constraint.

The program has a built-in library of constraint templates. These are the grammatical forms of commonly encountered constraints but with some entries pre-set.

These templates can be used as a short cut in constructing commonly encountered constraints.

There are four kinds of constraints:
1—Time Limits
2—Conditional Constraints
3—Preferences
4—Regularity.

Time Limits

Each Time Limit expresses a limitation on the amount of time or number of assignments that one or more employees can be scheduled to work, counting those assignments with a specified class of shifts and to a specified class of slots within a specified class of calendars.

Examples of Time Limits are 'Each nurse works at least 10 and no more than 40 hours in every 6 week interval, counting only the emergency room shift and only time worked on weekends and holidays,' or 'The total number of hours worked by all the junior surgical residents on any weekend is between 100 and 200 hours.'

Each Time Limit may have the following elements:

Employee Class: The user specifies the employees to whom the Time Limit applies either by selecting those employees from a list, by selecting a pre-existing Employee Class, or by specifying acceptable values of one or more employee attributes. The default value is 'all employees.'

Interval Length: The user specifies an integer and chooses from among 'hours', 'days,' 'weeks,' and 'months.' This specifies the time interval over which the Time Limit applies.

Shift Class: The user specifies a class of one or more shifts which are to be counted in satisfying the Time Limit. The default value is 'all shifts'.

Slot Class: The user specifies a class of one or more slots which are to be counted in satisfying the Time Limit. The default value is 'all slots'.

Calendar Class: The user specifies a class of one or more calendars, thereby specifying which days worked are to be counted in satisfying the Time Limit. The default value is 'every day.'

Unit of Time Measurement: The user chooses from among 'minutes,' 'hours,' 'days,' 'weeks,' 'months,' 'shifts,' and 'rotations.' This choice specifies the size of the units of time counted in the Time Limit.

Range: The user chooses at least one of two integers—the upper and lower limits of a numeric range. The user also chooses operators to describe this range at its limits. The operator for the lower limit is either 'greater than' or 'greater than or equal to' and the operator for the upper limit is either 'less than' or 'less than or equal to.'

If either limit is omitted, a default value is used. The default value for the lower limit is zero. The default value for the upper limit is 'unlimited.'

This range specifies the number of time units that may be worked in any interval of the specified interval size.

A switch, 'Each'/'As a Group': If the switch is set to 'Each,' the Time Limit applies to each of the specified employees individually. If the switch is set to 'As a Group' the Time Limit applies to the sum of the times worked by the class of specified employees as a whole.

Conditional Constraints

Each Conditional Constraint expresses a restriction on acceptable schedules of the form 'if a certain pattern of work assignments occurs in the schedule, then another must (or must not) occur.'

Some examples of Conditional Constraints are:

If a doctor works three days in a row, he doesn't work the next two days.

If Al works during any weekend between July 1 and August 31, Susan does not work during the same weekend If two union members work together on at least three Saturday mornings in three consecutive months and a different union member works every Sunday in one of those three months, then some other union member works at least three emergency room shifts in each of the next two months Each Conditional Constraint is designated by the user as either a 'weak' or 'strong' Conditional Constraint, and the user may toggle a Conditional Constraint between these two designations. Strong Conditional Constraints must be satisfied in any acceptable schedule. Weak constraints may be violated, although the automatic scheduling algorithm is designed so that they will be satisfied in most cases.

Conditional Constraints are specified by a formal grammar and comprise a limited programming language. However the system is structured so that the user creates Conditional Constraints by making a series of choices and selections from lists, rather than by creating program code. As a constraint is constructed, an English language translation of the constraint is simultaneously constructed and displayed. The user is thus shielded from the complexity of the underlying programming language and no programming skill is required to use the system.

In one embodiment of the invention, the user has access to a simplified and restricted version of the full Conditional Constraint construction mechanism, in addition to his access to the full Conditional Constraint construction mechanism. These simplified versions are of two types:

1—The user is presented with structured and indexed lists of frequently occurring forms of Conditional Constraints, each form having only a few variable parts to be specified. For instance, the user is presented with the form:

'Employees in <Employee Class> don't work <N> days in a row.'

The system will automatically turn this form into a Conditional Constraint once the user specifies values for the Employee Class and the integer N.

2—The user is presented with the Conditional Constraint composition screen, but with certain 'advanced' features unavailable. Such advanced features that may be unavailable include the 'N As A Group' construct for employees, and parts B and D of the Duration Specifier (see below).

Each Conditional Constraint contains an optional 'If' part and a required 'Then' part. Whenever a schedule satisfies all the conditions in the 'If' part of the constraint it must also satisfy all the conditions in the 'Then' part. The 'If' part of a constraint may be empty; in that case, the 'Then' part of the constraint must be satisfied by the schedule unconditionally.

The 'If' part of a Conditional Constraint consists of an unlimited number of clauses. For the 'If' part of a Conditional Constraint to be satisfied by a schedule, all these clauses must be simultaneously satisfied by the schedule. The 'Then' part of a Conditional Constraint consists of a single clause.

In some embodiments of the invention, the Conditional Constraint language may be extended to permit clauses to be connected with an 'or' connective as well as an 'and' connective, and also to permit the 'Then' part of a constraint to contain an arbitrary number of clauses.

A clause describes a class of employees and a temporally structured pattern of times and/or shifts, and asserts that some or all of the described employees work (or don't work) within the described temporal pattern. Therefore, each clause has two principal components—an Employee Pattern and a Time Pattern. A third component of the clause, the connective, bridges the Employee Pattern and the Time Pattern.

Tools for constructing and manipulating Conditional Constraints include:

1—Create a new clause,
2—Delete one or more clauses, and
3—Copy one or more clauses.

Employee Pattern

The Employee Pattern of a clause has two parts.

The first part of the Employee Pattern, the 'Employee Class' describes the set of employees to which the clause refers. The Absolute Employee Class Specifier of a clause may designate a class of employees without reference to the employee class of a preceding clause in the same constraint—an Absolute Absolute Employee Class Specifier—or in relation to the Employee Class of a preceding clause in the same constraint—a Relative Absolute Employee Class Specifier. If a clause is the first clause in a constraint, it can contain only an Absolute Absolute Employee Class Specifier.

An Absolute Absolute Employee Class Specifier for a clause designates a class of employees using the same mechanisms as in the description of the Employee Class of a Time Limits Constraint above; thus a class of employees may be designated by listing its members, by restricting membership to employees who have certain attribute values, or by importing a previously defined Employee Class.

A 'Relative Absolute Employee Class Specifier' designates a class of employees for a clause in relation to the Employee Class of an earlier clause of the constraint. For example, if the preceding clause says:

'. . . Three nurses work on a Wednesday' those three nurses comprise an Employee Class that can be referenced by a subsequent clause that says:

'. . . the same employees work on the following Friday'

A relative employee class can depend on the employee class of a preceding clause in more complex ways, e.g.:

'. . . Two nurses, not among the three who worked Wednesday, work on the following Friday.'

A Relative Employee Class is created by choosing a preceding clause in the same constraint so as to select the Employee Class that is being referred to, and selecting one of:

1—Same employees as Employee Class of reference clause
2—All employees not in Employee Class of reference clause.
3—Employees whose assignments caused the reference clause to be satisfied
4—Employees other than those whose assignments caused the reference clause to be satisfied
5—Employees in the Employee Class of the reference clause other than those whose assignments caused the reference clause to be satisfied
6—Employees specified by relative attribute values.

In the example above, the classes of employees defined by these selections are:
1—All nurses
2—All employees who aren't nurses
3—The three nurses who worked on Wednesday
4—All employees except for the three nurses who worked on Wednesday
5—All nurses except for the three nurses who worked on Wednesday
6—If this selection is made, the user selects one or more attributes for employees, and describes acceptable values for those attributes relative to the attribute values of the employees in the employee class of the reference clause. For example, the user could specify the class of nurses with more seniority than any of the three nurses who worked on Wednesday.

In constructing a Relative Employee Class, the user has the option of selecting which of the preceding clauses in the constraint is being referred to. The default selection is the nearest preceding clause using an Absolute Employee Specifier. The user has a similar option for the other Relative Class constructions described below.

The second part of the Employee Pattern describes the pattern of use of the employees in the Employee Class. This second part is created by choosing one of:
1—Each If this option is chosen, the clause applies individually to every employee in the Employee Class. The clause is satisfied only if the condition on employee assignments specified by the remainder of the clause is satisfied by each employee in the Employee Class.
2—Each of Range of above If this option is chosen, the user specifies at least one of a minimum and maximum value of an integer range. The clause is satisfied only if the number of employees in the Employee Class of the clause that satisfies the condition on employee assignments specified by the remainder of the clause is in the specified range.
3—Range total If this option is chosen, the user specifies at least one of a minimum and maximum value of an integer range. The clause is satisfied only if the total number of employees in the Employee Class working throughout the time specified by the clause's Time Pattern is in the specified range.

A clause with this option imposes no further requirements on the employees working at any instant and, in particular, does not require that the same employees work throughout the time specified, nor that the same group of employees work together throughout.
4—N as a group If this option is chosen, a total of N employees from the Employee Class is selected. The clause is satisfied only if the times that those N employees are all working satisfies the condition on work assignments specified by the remainder of the clause. The user specifies the value of N.

For example, if the Employee Class is 'doctors' and remainder of the clause is 'works three Saturdays in March' then the clause constructed with each of the above choices is
1—'Each doctor works three Saturdays in March.'
2—'At least 4 and (less) no more than 7 doctors each work three Saturdays in March.' (Range is 4-7)
3—'On three Saturdays in March, between 4 and 7 doctors are working.' (Range is 4-7)
4—'There is a (team) group of 4 doctors who all work on the same three Saturdays in March.' (N=4)

For options 2, 3, and 4 above, whether or not the clause is satisfied will depend on which employees are chosen, and the group of employees chosen may be referenced by subsequent relative employee specifiers in the constraint. In effect, Conditional Constraints with such variable parts in one or more of their clauses, create a family of constraints, one for each way of assigning objects to the variable parts that satisfies all the clauses in the 'If' part of the constraint.

For example, in the constraint
'If some (one) doctor works any (one) day, then the same employee does not work the next day'
there are two variable parts, one permitting the substitution of any doctor, and one permitting the substitution of any day. If there were 10 doctors and 50 days to be scheduled, the effect of this constraint is as if 500 similar constraints without variable parts existed—one for every doctor and every day.

Connective

To indicate the connective of a clause, the user chooses either:
1—Work(s)
2—Doesn't work Time Pattern The Time Pattern of a clause describes a pattern of times and shifts, and slots that the employees described by the Employee Pattern must or must not be assigned to work to satisfy the clause. The Time Pattern has four parts: a Calendar Class, a Shift Class, a Slot Class and a Duration. The Duration describes a temporal pattern to be worked. The Calendar Class, Shift Class and Slot Class describe which calendar days, shifts and slots are counted within the temporal pattern specified.

Calendar Class

The Calendar Class gives the user a filtering mechanism to describe which calendar days occur within the time specified. The Calendar Class can be described by either an Absolute Calendar Class Specifier or a Relative Calendar Class Specifier.

An Absolute Calendar Class is specified either by selecting a previously defined Calendar Class or by selecting any number of calendars. If this latter option is chosen, the user specifies whether the Calendar Class is the union or intersection of the selected calendars. The default Calendar Class is the 'every day' calendar.

A Relative Calendar Class is specified by selecting a preceding reference clause in the constraint and specifying whether the Calendar Class of the present clause is
1—identical to the Calendar Class of the reference clause
2—the complement of the Calendar Class of the reference clause
3—those days on which assignments took place that caused the reference clause to be satisfied
4—all days other than those days on which assignments took place causing the reference clause to be satisfied
5—all days in the Calendar Class of the reference clause other than those on which assignments took place causing the reference clause to be satisfied.

For example, if the reference clause is
'Joe works (some) 2 Saturdays'
and for some instantiation of variable parts this clause was satisfied because Joe is assigned to work February 7 and February 21, the Relative Calendar Classes defined by the above options are
1—all Saturdays
2—all days except Saturdays
3—February 7 and February 21
4—all days except February 7 and February 21
5—all Saturdays except February 7 and February 21

Shift Pattern

The Shift Pattern describes the class of shifts to which the clause refers, and how those shifts are combined. The first part of the Shift Pattern, the Shift Class is either an Absolute Shift Class or a Relative Shift Class. An Absolute Shift Class is defined either by selecting a pre-defined Shift Class, by choosing shifts from a list, or by selecting shifts according to their attribute values.

A Relative Shift Class is specified by selecting a preceding reference clause and selecting one of:
1—Same shifts as reference Shift Class
2—Shifts not in reference Shift Class
3—Shifts with assignments that caused the reference clause to be satisfied.
4—Shifts other than those with assignments that caused the reference clause to be satisfied
5—Shifts in the reference Shift Class other than those with assignments that caused the reference clause to be satisfied.

The second part of the Shift Pattern describes how the members of the Shift Class determine whether a clause is satisfied. This part is selected from:
1—'Each'
If this option is chosen, the clause is satisfied if the condition on shifts defined by the remaining parts of the clause is satisfied by each member of the Shift Class individually.
2—'Each of Range of the above.'
If this option is chosen, the user enters at least one of a minimum and maximum value defining an integer range. A set of N members of the Shift Set is selected. The clause is satisfied if the number of shifts in the Shift Class that satisfy the condition on shifts defined by the remaining parts of the clause is in the range.
3—'All'
If this option is chosen, the union of the members of the Shift Class is considered as a single shift. The clause is satisfied if it is satisfied by this single unified shift.
4—'All of N of above'
If this option is chosen, a set of N members of the Shift Class is selected. The union of these N shifts is then considered as a single shift. The clause is satisfied if it is satisfied by this single unified shift.
For example, if the rest of the clause says 'Joe works . . . 5 days in March' and the Shift Class is the morning evening and graveyard shift then the above choices correspond to the following clauses
1—'Joe works 5 days in March on the morning shift, 5 days in March on the evening shift and 5 days in March on the graveyard shift.'
2—'Of the 3 shifts—the morning, evening and graveyard—Joe works 5 days in March on either 1 or 2 of them.' (Range=1 to 2)
3—'Joe works 5 days in March counting all his work on any of the morning, evening, and graveyard shifts.'
4—'Joe works 5 days in March, counting all his work on some 2 of the morning, evening, and graveyard shifts.' (N=2)

Duration

The Duration of a clause describes a pattern of times to be worked. A pattern of time consists of one or more specified intervals of time. A Duration may be either absolute or relative. An Absolute Duration is a duration that does not refer to the duration of a preceding clause. A Relative Duration is a Duration that refers to the duration of a preceding clause.

An Absolute Duration has three parts, a Fine Pattern, a Large Pattern, and an optional Date Range. The Fine Pattern is a finely detailed amount and pattern of time. The Large Pattern is a coarser pattern within which the Fine Pattern is distributed.

Examples of Fine Patterns are:
'3 consecutive shifts'
'5 of the first 7 days'
'the $4^{th}$ rotation'

Examples of Large Patterns are:
'2 of the first 5 weeks'
'4 consecutive weeks'
'the first 6 months of the year'

For example, an Absolute Duration might describe, 'four consecutive days in each of three consecutive months.' In this example, the Fine Pattern is 'four consecutive days' and the Large Pattern is 'each of three consecutive months.'

The Date Range limits the Duration to the interval between a Start and End Date.

Fine Pattern

A Fine Pattern is described by choices from each of three lists, the Quantifier List, the Order List and the Object List.

The choice from the Quantifier List specifies the number of the objects selected from the Object List. The Quantifier List contains the following options:

1—'Each'—
If 'each' is chosen every one of the objects chosen from the Object List that are within the range specified by the Order List is in the Fine Pattern.
2—'Some #'—
The user enters an integer N and some N of the objects chosen from the Object List, and also within the range specified by the Order List, are in the Fine Pattern
3—'Some # Consecutive'—
This choice has the same effect as 'Some #', with the additional restriction that the N objects selected must be temporally consecutive.

For the Quantifier List, 'Each' is the default value.

The Order List restricts the possible choices of objects from the Object List. The Order List contains the following options:

1—'All'—
If 'All' is chosen no further restriction is placed on the choice of objects.
2—'Range'—
If 'Range' is chosen the user enters at least one of an upper and lower limit of an integer range. This integer range applies to the temporal order of the objects and restricts the choice of objects to those within the range. If the lower and upper limits of the range are equal, the choice of objects is restricted to the $N^{th}$ object in temporal order, or to objects at more than, less than, etc., the $N^{th}$ temporal position, depending on the operator selected.
3—'First #'—
If 'First #' is selected, the user enters an integer, N. The choice of objects selected is restricted to the first N objects in temporal order.
4—'Last #'—
If 'Last #' is selected, the user enters an integer, N. The choice of objects selected is restricted to the last N objects in temporal order.

For the Order List 'All' is the default value.

The selections on the Object List specify the size of the time pattern. The selections are:
  1—'Instances'—
  If 'Instances' is chosen, the objects are occurrences of a shift in the Shift Class of the clause.
  2—'Hours'—
  If 'Hours' is chosen, the objects are hours of work. The total number of hours is counted, regardless of when the hours begin on the clock. So, for example, the time from 3:30 to 4:30 P.M. is one hour not (parts of) two hours.
  3—'Days'—
  If 'Days' is chosen, the objects are days beginning and ending at midnight. A day is counted as worked if an employee works at any time during the day.
  If 'Some # Consecutive' and N is chosen from the Quantifier List and 'Days' is chosen from the Object List, then N numerically consecutive days are specified.
  4—'Calendar Days'—
  If 'Calendar Days' is chosen, the objects are days, but only days within the Calendar Class of the clause.
  If 'Some # Consecutive' and N is chosen from the Quantifier List and 'Calendar Days' is chosen from the Object List, then N days that occur consecutively within the Calendar Class are specified. These N days need not actually be consecutive. For example, if the Calendar Class includes only Sundays, and 'Some # Consecutive' and '5' are chosen, then the Fine Pattern is 5 consecutive Sundays.
  5—'Rotations'—
  If 'Rotations' is chosen, the objects are rotations of any members of the Shift Class of the clause. A rotation is counted as having been worked if any instance within the rotation has been worked.
  6—'Weeks'—
  If 'Weeks' is chosen, the objects are weeks, i.e., 7 day periods starting on a particular day of the week. (The start day of the week is selected by the user in the initial setup of the system. The default start day is Sunday.) A week is counted as having been worked if an employee works at any time within the week.
  7—'Months'—
  If 'Months' is chosen, the objects are calendar months. A month is counted as having been worked if an employee works at any time within the month.
  8—The last option for the Object List requires making a choice from each of two sublists, then specifying an integer N, and an operator.
  Options for the first sublist are 'Day', 'Week', 'Month' and 'Rotation.' Options for the second sublist are Week, Month and Year. Once an object is chosen from the first sublist, only larger objects can be chosen from the second sublist. For instance, if 'Week' is chosen from the first sublist, then only 'Month' or 'Year' can be chosen from the second sublist.
  The integer N and operator specify which objects from the first sublist within each object from the second sublist are counted. So, for example, if 'day', 'month' '12' and '<=' are chosen, the objects selected are the first twelve days in the month.
  The default choice for the Object List of Part A is 'Instances'.

Large Pattern

The Large Pattern of a Duration is a larger time pattern within which the Fine Pattern is distributed. A Large Pattern is created by making a selection from each of three lists, the Quantifier List, the Order List and the Object List. (These lists are distinct from the lists for the Fine Pattern, above.)

The first list for specifying a Large Pattern, the Quantifier List, specifies the number of objects selected from the Object List. The Quantifier List contains the following options:
  1—'Anytime'—
  If 'Anytime' is chosen there is no restriction on when the Fine Pattern occurs. If 'Anytime' is chosen no choices are made from the Order List and Object List.
  2—'Each'—
  If 'Each' is chosen, the Fine Pattern must occur in every one of the objects chosen from the Object List and within the range specified by the Order List.
  3—'Each of Some #'—
  If 'Each of Some #' is chosen, the user enters an integer, N. The Fine Pattern must occur in each some N objects chosen from the object list and within the range specified by the Order List.
  4—'Each of Some # Consecutive'—
  This choice has the same effect as 'Some #', with the additional restriction that the N objects selected must be temporally consecutive.
  5—'Total # Consecutive'—
  If 'Total # Consecutive' is chosen the user enters an integer, N. is specified, then some N temporally consecutive objects chosen from the Object List are selected. The Fine Pattern must occur at least once in every N consecutive objects chosen from the Object List and with the range specified by the Order List.

The default choice for the Quantifier List of the Large Pattern is 'Anytime'.

The Order List of the Large Pattern restricts the possible choices of objects. The options on the Order List are:
  1—'All'—
  If 'All' is chosen no further restriction is placed on the choice of objects.
  2—'Range'—
  If 'Range' is chosen the user enters at least one of the upper and lower limits of an integer range. This integer range applies to the temporal order of the objects and restricts the choice of objects to those within the range. If the values for the lower and upper limits of the range are the same, both N, the choice of objects is restricted to the $N^{th}$ object in temporal order, or to objects at more than, less than, etc., the $N^{th}$ temporal position, depending on the operator selected.
  3—'First #'—
  If 'First #' is selected the user enters an integer, N. The choice of objects selected is restricted to the first N objects in temporal order.
  4—'Last #'—
  If 'Last #' is selected the user enters an integer, N. The choice of objects selected is restricted to the last N objects in temporal order.

For the Order List 'All' is the default value.

The options on the Object List of the Large Pattern, specify the size of the time pattern used. The options are the same as for the Object List of the Fine Pattern, except that the option 'Instances' is omitted and the option 'Years' is added. Thus, the options are
  1—'Hours'
  2—'Days'.
  3—'Calendar Days'
  4—'Rotations'
  5—'Weeks'

6—'Months'
7—'Years'
8—A choice from each of two sublists, analogous to choice 8 for the object list of the Fine Pattern.

The default choice for the Object List for the Large Pattern 'Days'.

The Date Range of the duration specifies the range of dates from which intervals making up the Fine Pattern can be chosen. If no Start/End Date is selected, the default dates are the Start/End Dates of the constraint, if they exist. Otherwise, the default dates are the Start/End Dates of the scheduling problem.

Relative Durations

Durations can be absolute or relative. An Absolute Duration specifies a temporal pattern without reference to durations in earlier clauses. A Relative Duration specifies a pattern of intervals that stand in a specified relationship to the duration of a preceding clause. Examples of Absolute Durations are 'one shift on each of two consecutive days' and 'every day from March 10 to March 17.' Examples of Relative Durations are 'the next rotation' and 'the first Tuesday in the next month.'

If a clause is a second or later clause in a constraint, the duration specified within that clause can be relative or absolute. Thus, the user has available all the means for constructing an absolute Fine Pattern as well as means for constructing Relative Fine Patterns. Similarly the user has available all the means for constructing absolute Large Patterns, as well as means for constructing Relative Large Patterns.

The Date Range of a Relative Duration has one additional option, 'same date range as reference duration.'

Relative Fine Pattern

To describe a Relative Fine Pattern, the user selects a preceding reference clause and one item from each of: The First Quantifier List; The Relation List; The First Object List; The Second Quantifier List; and The Second Object List.

The meaning of these five parts and how they together specify a Relative Fine Pattern of time intervals is explained in reverse order below. In outline, the selections made from the Second Quantifier list and the Second Object list are used to construct a pattern of time intervals by referring to the intervals comprising the fine pattern of the reference clause. The Second Quantifier list describes the number and arrangement of time units in this pattern and the Second Object list describes the size of the time units. Together, the choices from these two lists create a set of intervals 'R', the 'Reference Set.'

The choices from the first three lists—the First Quantifier List, the Relation List and the First Object List—specify the Relative Fine Pattern as a set of intervals or instances that stand in a specified temporal relation to the members of the set R.

Suppose that the Fine Pattern of the reference clause is a set 'S' of instances or time intervals. This set S can be described as a set of time units of any of several sizes. That is, it can be re-described as a set S*—a set of hours, or a set of instances, or a set of days, weeks, months or years—where an hour, a day, week, month, or year is included in S* if any part of S occurs within that hour, day, week, month, or year.

The entries for the Second Object List, correspond to these ways of re-describing the set S. They are (1) 'Instances'; (2) 'Hours'; (3) 'Days'; (4) 'Weeks'; (5) 'Months'; (6) 'Years'.

The entries in the Second Quantifier List specify the reference set R as a subset of S*. They are:
1—'First #'
If 'First #' is chosen the user enters an integer, N. R is the temporally first N members of S*.
2—'Last #'
If 'Last #' is chosen the user enters an integer, N. R is the temporally last N members of S*
3—'Each'
If 'Each' is chosen, R is S*
4—'Some #'
If 'Some #' is selected the user enters an integer, N. R is a set of some N members of S*.
5—'Some # Consecutive'
This option is like 'Some #' with the further restriction on R that the set of N objects be temporally consecutive.
6—'Range'
If 'Range' is selected the user is prompted for two integers, the upper and lower limits of an integer range. If M and N are the limits, the set R is the $M^{th}$ through $N^{th}$ members of S*.

The user's choices from the first three lists for defining a Fine Pattern, combined with the reference set R, construct the Relative Fine Pattern.

This construction occurs in two stages. First, the choices from the Relation List and the First Object List create a set, 'E', the set of objects initially eligible for inclusion in the Relative Fine Pattern. The size of the time units in E is specified by the choice from the First Object List, and membership in E is determined by R and the choice from the Relation List.

Lastly, the members of E included in the Relative Fine Pattern, are specified by the choice from the First Quantifier List.

The entries in the First Object List, specify the size of the time intervals in the set E. The options on the First Object List are:
1—'Instances'
2—'Calendar Instances'
Calendar Instances are only those instances that occur on days in the Calendar Class of the clause.
3—'Hours'
4—'Days'
5—'Calendar Days'
Calendar Days are only those days that occur on days in the Calendar Class of the clause.
6—'Rotations'
7—'Weeks'
8—'Months'
9—'Years'

The options for the Relation List define the set E by specifying time intervals in E by their temporal relationship to the members of the Reference Set, R. The options for the Relation List are:
1—'Before'
If 'Before' is selected, the set E includes only time intervals or instances that end before every member of the set R begins.
2—'After'
If 'After' is selected, the set E includes only time intervals or instances that begin after every member of the set R ends.
3—'Previous #'
If 'Previous #' is selected the user enters an integer, N. For each member of R, the N objects of unit size specified by the First Object List temporally preceding that member of R are in the set E.
4—'Next #'
If 'Next #' is selected the user enters an integer, N. For each member of R, the N objects of unit size specified by the First Object List temporally following that member of R are in the set E.

5—'Different'

If 'Different' is selected, only time intervals or instances that do not temporally overlap any member of the set R are in the set E.

6—'Previous Contiguous'

If 'Previous Contiguous' is selected, time intervals or instances are in the set E only if they end exactly when some member of the set R begins.

7—'Next Contiguous'

If 'Next Contiguous' is selected, time intervals or instances are in the set E only of they begin exactly when some member of the set R ends.

8—'Earlier by #'

If 'Earlier by #' is selected the user enters an integer, N. The time intervals or instances in the set E are those which are Nth earlier, counting time units of the size chosen from the First Object List, than some member of the set R.

9—'Later by #'

If 'Later by #' is selected the user enters an integer, N. The time intervals or instances in the set E are those which are Nth later, counting time units of the size chosen from the First Object List, than some member of the set R.

10—'Overlapping'

If 'Overlapping' is selected, time intervals or instances are in the set E only if they temporally overlap a member of the set R.

11—'Identical'

If 'Identical' is selected, the set E is the same as the set R. This option is available only if the time unit sizes chosen from the First and Second Object Lists are the same.

12—'Included In/Including'

If 'Included In/Including' is selected, and the time unit chosen from the First Object List is larger than the time unit chosen from the Second Object List, then a time interval or instance is in E only if it temporally includes some member of R. If the time unit chosen from the First Object List is smaller than the time unit chosen from the Second Object List, then a time interval or instance is in E only if it is temporally included in some member of R. This option is available only if the choices from the First and Second Object Lists differ.

The options on the First Quantifier List allow the user to specify which members of the set E are actually included in the Fine Pattern. The options on the First Quantifier list are:

1—'Anytime'

If 'Anytime' is chosen, no restriction is placed on the intervals selected, and no further choices are made in specifying the Relative Fine Pattern.

2—'Each'

If 'each' is chosen, the Fine Pattern is identical to the set E.

3—"Some #"

If 'Some #' is selected, the user enters an integer, N. The Fine Pattern is a set of some N members of the set E.

4—'Some # consecutive'

If 'Some # consecutive' is selected, the user enters an integer, N. The Fine Pattern is a set of some N temporally consecutive members of the set E.

'Anytime' is the default selection for the First Quantifier List.

Relative Large Pattern

The mechanism used to construct relative large time patterns, is almost identical to the mechanism used to construct relative small time patterns. A reference set, R, is derived from the large time pattern of a preceding clause, then a set E of intervals bearing a temporal relation to members of R, and the Relative Large Pattern is selected from E.

The only differences between the construction of a Relative Fine Pattern and a Relative Large Pattern are:

1—The reference set R is constructed from a preceding large time pattern rather than from a preceding small time pattern. (Note that the reference sets for the Fine Pattern and the Large Pattern of a clause can come from different preceding clauses. For example, in the constraint 'If some doctor works a dayshift and some nurse works any shift on a Tuesday, then Joe works each day after the doctor works in each week that the nurse works' the Then' clause has a time pattern with a Relative Fine Pattern (each day after the doctor worked) and a Relative Large Pattern ('each week that the nurse works') derived from the first and second clauses respectively a time pattern with a Relative Fine Pattern and a Relative Large Pattern)

2—The options 'Instances' is omitted from the First Object List of for the Large Pattern.

Preferences and Optimization

There are three kinds of scheduling preferences:

1—Optimization Preferences—these direct the automatic scheduling algorithm to maximize or minimize the total of an attribute value or other 'Objective Function,' summed over some set of assignments in a schedule.

2—Specification, by the employer, of preferred employees for assignment to certain shifts, slots and times.

3—Preferences expressed by employees for specific work assignments.

Preferences of all three types can potentially conflict with one another, and the system provides a mechanism for resolving these conflicts. In one embodiment of the system, all three kinds of preferences associated with a scheduling problem are maintained on a single list which can be reordered by the user. When two Preference Constraints conflict, for an assignment, the Preference Constraint higher on the list is used and the Preference Constraint lower on the list is ignored for that assignment.

Optimization Preferences

To express an Optimization Preference the user can specify (step 110):

1—An Employee Class

2—A Calendar Class

3—A Shift Class

4—A Slot Class

5—An 'Objective Function'

The user defined 'Objective Function' of an optimization preference is an algebraic combination of one or more integer or numerical employee attributes. The objective function can be as simple as a single numerical attribute.

6—A switch—'Minimize'/'Maximize'

7—A second switch—'Avoid Missing Values'/'Prefer Missing Values.'

The meaning of an optimization preference is that the value of the Objective Function associated with each employee, summed over assignments for members of the Employee Class occurring within the Shift Class, Slot Class and Calendar Class should be minimized or maximized by the automatic scheduling algorithm. For example, an optimization preference can direct the automatic scheduling algorithm to seek a scheduling solution that minimizes the total payroll cost of a class of employees or that maximizes the sum of years of employee experience.

Some employees may not have values for the Objective Function because they are missing values for one or more of the attributes employed in the definition of the objective function. If 'Avoid Missing Values' is selected, the automatic scheduling algorithm will attempt to minimize the assignments of those employees. If 'Prefer Missing Values' is selected, the algorithm will attempt to maximize the assignments of these employees. For example, a factory may have some employees who are paid a fixed wage and other employees who are paid an hourly wage. If the employer sets up an optimization preference to minimize his payroll costs, they system will preferentially assign employees with lower hourly wage rates. The employees paid a fixed wage do not have an hourly wage. By choosing 'avoid' or 'prefer' missing value, the user tells the system whether to try to maximize or minimize the assignment of employees with a fixed salary.

Preferred Employees

To express a Preferred Employees Constraint, the user specifies:
1—An Employee Class
2—An (optional) Preference Ordering of that Employee Class.
   There are two ways for the user to construct a Preference Ordering:
   1—The user can manually order the list of employees within the Employee Class.
   2—The user can choose an employee attribute and specify the order of preference for the values of that attribute.
3—A Calendar Class
4—A Shift Class
5—A Slot Class A Preferred Employees Constraint directs the automatic scheduling algorithm to prefer employees in the Employee Class to other employees for assignments within each of the Calendar Class, the Shift Class, and the Slot Class, and that within the Employee Class, preference for these assignments should be made according to the Preference Ordering.

Employee Specified Preferences

To express an Employee Specified Preference the user specifies:
1—The name of an Employee
2—A Calendar Class
3—A Shift Class
4—A Slot Class
5—A switch—'Prefer'/'Avoid".

An Employee Specified Preference directs the automatic scheduling algorithm to minimize or maximize the assignments within each of the Calendar Class, Shift Class and Slot Class for a single employee. In some embodiments of the system, employees will be able to enter Employee Specified Preferences directly, whereas more global constraints will be entered by the employer or system administrator.

Regularity Constraints

To express a Regularity Constraint, the user specifies:
1—An Employee Class
2—A Shift Class.
3—A Slot Class
4—A Calendar Class The meaning of a Regularity Constraint is that, to the extent possible, each employee in the Employee Class should have a 'regular' or highly repetitive schedule of assignments within the Shift Class, Slot Class and Calendar Class. Whenever the automatic scheduling algorithm assigns an employee in the Employee Class to a qualifying slot-instance, the algorithm attempts to repeat this assignment for any unassigned instances of the same slot in the same shift and within the Calendar Class.

In other embodiments of the program, the expressive power of constraints is enlarged by permitting variable attribute values allowing attribute values across different types of objects, and across clauses in Conditional Constraints, to be matched and compared. For example, this feature permits creation of clauses like:

'No employee with security-clearance less than value x works in a slot with slot-security clearance value greater than or equal to x.'

Creation and Modification of Schedules

One embodiment of the invention has a facility for creating and storing scheduling problems and partial and complete solutions to scheduling problems. The system allows users to create, rename and delete scheduling problems. Users may save partially or completely solved scheduling problems and move from one problem to another, so that a user can work on more than one scheduling problem.

To create a scheduling problem the user specifies:
1—A starting date and ending date for the problem, and a Calendar Class of dates to be scheduled
2—A database of employees available to be assigned
3—A class of shifts to be scheduled
4—A class of slots to be scheduled Once a scheduling problem has been set up, the user may create new constraints and preferences or associate already created constraints and preferences with the problem.

Once a user has specified a scheduling problem, a class of slot-instances is created. A slot-instance is a request for one employee to work during a shift on a given date. Whenever a shift in the shift database for a scheduling problem occurs on a date in the calendar database for that scheduling problem, slot-instances are created for every slot associated with the shift which is also in the slot database for the scheduling problem. If the multiplicity of the slot is an integer N, N slot-instances are created for that shift, slot and date, signifying a request for N employees. If the multiplicity of the slot is a demand function F, N slot-instances are created, where N is the maximal value of F over all the days in the calendar database and in the rotation of the shift containing the date. (Because assignments take place one rotation at a time, if M employees are needed for the slot on one day in the rotation, M employees will be assigned throughout the rotation. This set of slot-instances over the course of a rotation is known as a rotation-instance.)

Solving a scheduling problem (step 132) consists of assigning an employee to each of these slot-instances in a way consistent with all the constraints, Time Limits and other restrictions inherent in the problem. Such an assignment of an employee to every slot-instance in the problem is a 'complete schedule' or a 'complete solution' to the scheduling problem.

However, at various stages in solving a scheduling problem, only some of the slot-instances may have an assigned employee. These states of partial assignment are 'partial schedules' or 'partial solutions' to the scheduling problem (202, see FIG. 2).

The state of the problem just after it has been set up, with no employee assigned to any slot-instance, is an 'empty schedule' or 'empty schedule problem solution.' In order to create a complete solution 142 to the scheduling problem, the user begins with an empty schedule and repeatedly modifies and builds partial schedules.

Two auxiliary functions—Verify 138 and Lock/Unlock are available to the user to assist him in this process.

Verify

At any point during the process of constructing a schedule solution the user can check whether the current partial or complete solution violates any active constraints, Time Limits, employee availability requirements and slot requirements. In general, constraint violations occur only after manual modification of schedule solutions, since the automatic scheduling algorithm rejects assignments that violate constraints or other conditions on the problem. Given a schedule solution, the verify function provides a list of all violations of every active constraint, Time Limit, employee availability requirement and slot requirement.

Lock/Unlock

Each assignment of an employee to a slot-instance in a schedule solution can exist in one of two states, 'Locked' or 'Unlocked'. If an assignment is locked, the automatic scheduling algorithm will not backtrack over that assignment as it searches for a complete schedule solution, unless explicitly instructed to do so. Attempts to manually modify the schedule that would change a locked assignment will cause a warning to appear. To manually modify a locked assignment, the user must take explicit action to override the lock.

There are two ways to change the Locked/Unlocked status of assignments:

1—Using any schedule display format (see below), the user may graphically select one or more assignments and lock or unlock all the selected assignments.

2—The user may select a class of employees, a class of shifts, a class of slots, a Calendar Class and a date range and lock or unlock all assignments for those employees to slot-instances within the Shift Class, Slot Class, and Calendar Class.

The locked/unlocked status of each assignment is displayed with a graphical icon in each schedule display format.

Schedule Modification

There are two ways to modify schedules, manually and automatically.

Manual Schedule Modification (Step 142)

Using any schedule display format, the user may select any slot-instance in the problem and view the list of employees who are available and qualified to fill that slot-instance, as well as lists of employees available but not qualified for that slot-instance, qualified but not available, and neither qualified nor available. The user can remove an assigned employee from a slot-instance, replace one employee with another, or assign an employee to an empty slot. Whenever the assignment of a slot-instance is modified, the user has the option to extend that modification to a larger class of slot-instances. To do so, he makes a choice from two lists of options. The first list is:

1—Extend modification throughout rotation.
  If this option is chosen, the modified assignment will be repeated in one slot-instance on each day of the rotation containing the date of the modification.
2—Extend modification forward.
  If this option is chosen, the modified assignment will be repeated in some instances of the slot on days following the date of the modification on which the shift occurs.
3—Extend modification backward.
  If this option is chosen, the modified assignment will be repeated in some instances of the slot on days preceding the date of the modification.
4—Extend modification forward and backward.
  If this option is chosen, the modified assignment will be repeated in some instances of the slot on days throughout the schedule.

The second list further specifies the set of slot-instances receiving the modified assignment. The options on the second list are:

1—Overwrite all.
  If this option is chosen, slot-instances already assigned an employee will have that assignment changed to the new assignment if the change is necessary to fulfill the action specified by the first list
2—Overwrite unlocked only.
  If this option is chosen, only unlocked assignments will be changed to fulfill the action specified by the first list.
3—Don't overwrite.
  If this assignment is chosen, no overwriting takes place. Only unassigned slot-instances can be assigned to fulfill the action specified by the first list
4—Examine sequentially.
  If this option is chosen, the slots instances eligible to be modified by the action specified by list 1 are shown to the user in sequence, so that he can decide whether or not to modify the assignment of each of these slot-instances The user is also warned whenever one of his manual assignments violates an active Constraint or Time Limit.

Automatic Schedule Modification

At any point after a scheduling problem has been specified, the user can deploy the system's automatic scheduling algorithm to go from an empty schedule solution or partial schedule solution to a complete schedule solution 142. For example, the user can manually enter the schedule assignments for a specific day or week, or the assignments for a specific employee or group of employees, and direct the scheduling algorithm to generate a complete schedule that includes his manual entries.

The user can also require that a schedule solution be consistent with a temporally preceding schedule solution or attendance record for some or all of the same employees, shifts and slots. For example, if a Time Limit requires that no nurse work more than 3 Saturdays in any two months, and nurse J has actually worked 2 Saturdays in February, this feature would insure that nurse J was assigned no more than 1 Saturday in March.

If applied to a scheduling problem with an empty schedule, the automatic scheduling algorithm will search for and, if possible, generate a complete schedule consistent with the problem's constraints. If no such schedule exists—because of conflicts among the problem's constraints and requirements—the algorithm will produce as nearly complete a partial schedule as possible and indicate why the schedule cannot be completed.

If the automatic scheduling algorithm is applied to a scheduling problem with a partial schedule, the algorithm will search for and, if possible, generate a complete schedule that contains all the locked assignments in the partial schedule.

Parameters for the Automatic Scheduling Algorithm

Prior to starting the automatic scheduling algorithm, the user enters several parameters that further describe the problem to be solved. These parameters are:

1—A Start and End Date. These two dates must lie within the Start and End Dates of the original problem, and further delimit the problem to be scheduled. For example, an employer might set up his scheduling problem for an entire year, but then use this feature to solve the problem a month at a time. The default value for the Start Date parameter is the current date if the current date is within the date range of the problem, otherwise the default Start Date parameter is the Start Date of the problem. The default End Date parameter is the End Date of the scheduling problem.

2—An Employee Class, a Calendar Class, a Shift Class, and a Slot Class. These classes further delimit the employees and slot-instances to be assigned. In each case, the default value is 'all.'

3—A choice to begin from an empty schedule, to begin from current locked assignments only, or from all current assignments. If either of the latter two options is chosen, the user also indicates whether or not the algorithm can backtrack over (i.e., modify) all current assignment, unlocked current assignments only, or no current assignments.

4—A choice of one or more schedule solutions or attendance records temporally preceding the Start Date parameter. If more than one of these preceding schedules or records is selected, they must not contain conflicting assignments, and this is automatically checked.

5—A Search Depth parameter. The value of this parameter specifies how extensive a search for scheduling solutions to undertake. Higher values of the parameter produce more extensive searches. More extensive searches are more likely to find an acceptable scheduling solution or a nearly acceptable partial solution but take longer to execute. The search depth is a choice between a user—entered positive integer and 'unlimited.'

In one embodiment of the invention, if the search depth is the integer n, the search for a schedule solution is limited by permitting only N failed attempts at assigning an employee to a rotation-instance before backtracking to an earlier assignment, thereby limiting the breadth of the algorithm's search tree. In another embodiment of the program, if the search depth is the integer N, the algorithm will backtrack over only N assignments before declaring a rotation-instance 'unfillable' and moving on to the remaining unassigned rotation-instances. Combinations of these two strategies can also be used. If the search depth is 'unlimited,' there is no restriction on the search.

In alternative embodiments of the invention, the search depth is variable, not a constant, and depends on the number of employees eligible and available for a rotation-instance, the point in the search at which the rotation-instance is encountered, the amount of time used thus far by the algorithm, and other factors.

1—A 'fill optional slots' parameter, specifying a class of optional slots to fill. This class is specified by a choice of
   a—Fill all optional slots. If this choice is made, the algorithm attempts to fill all optional slots after as many required slot-instances as possible have been assigned and as many minimum Time Limits as possible have been reached (see below)
   b—Fill no optional slots. If this choice is made, the algorithm halts after as many required slot-instances as possible have been assigned and as many minimum Time Limits as possible have been reached
   c—Fill class of optional slot, where the class of optional slot is specified by a Slot Class, a Shift Class, and a Calendar Class. If this choice is made, the algorithm attempts to fill all optional slot-instances in the Slot Class, associated with a shift in the Shift Class, and occurring on a day in the Calendar Class, after as many required slot-instances as possible have been assigned and as many minimum Time Limits as possible have been reached The default value of the 'Fill optional slots' parameter is 'Fill no optional slots.'

Automatic Scheduling Algorithm

Figure 2A:
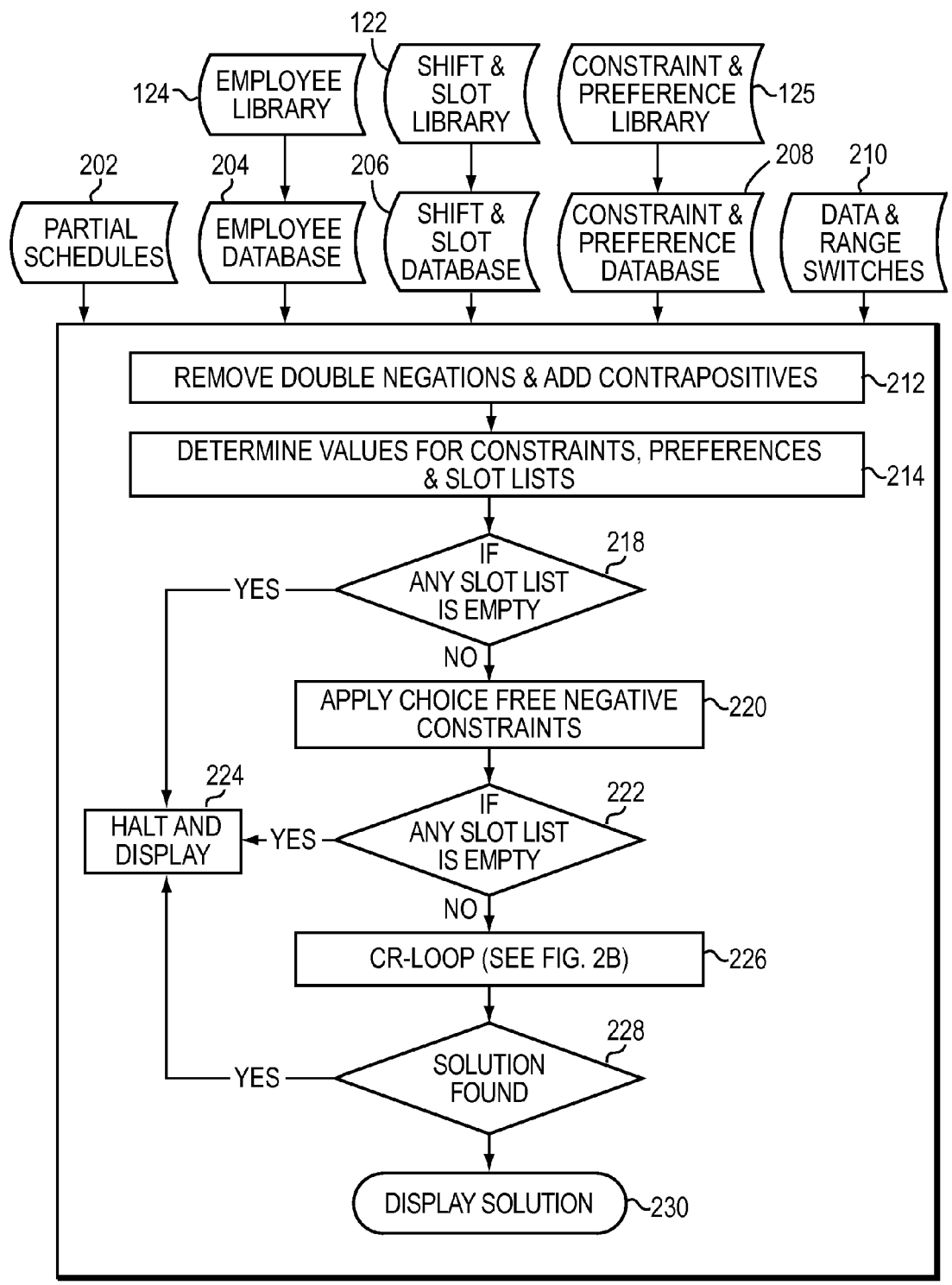
FIGS. 2a-2b are a flow chart of a scheduling algorithm for resource scheduling.
Figure 2B:
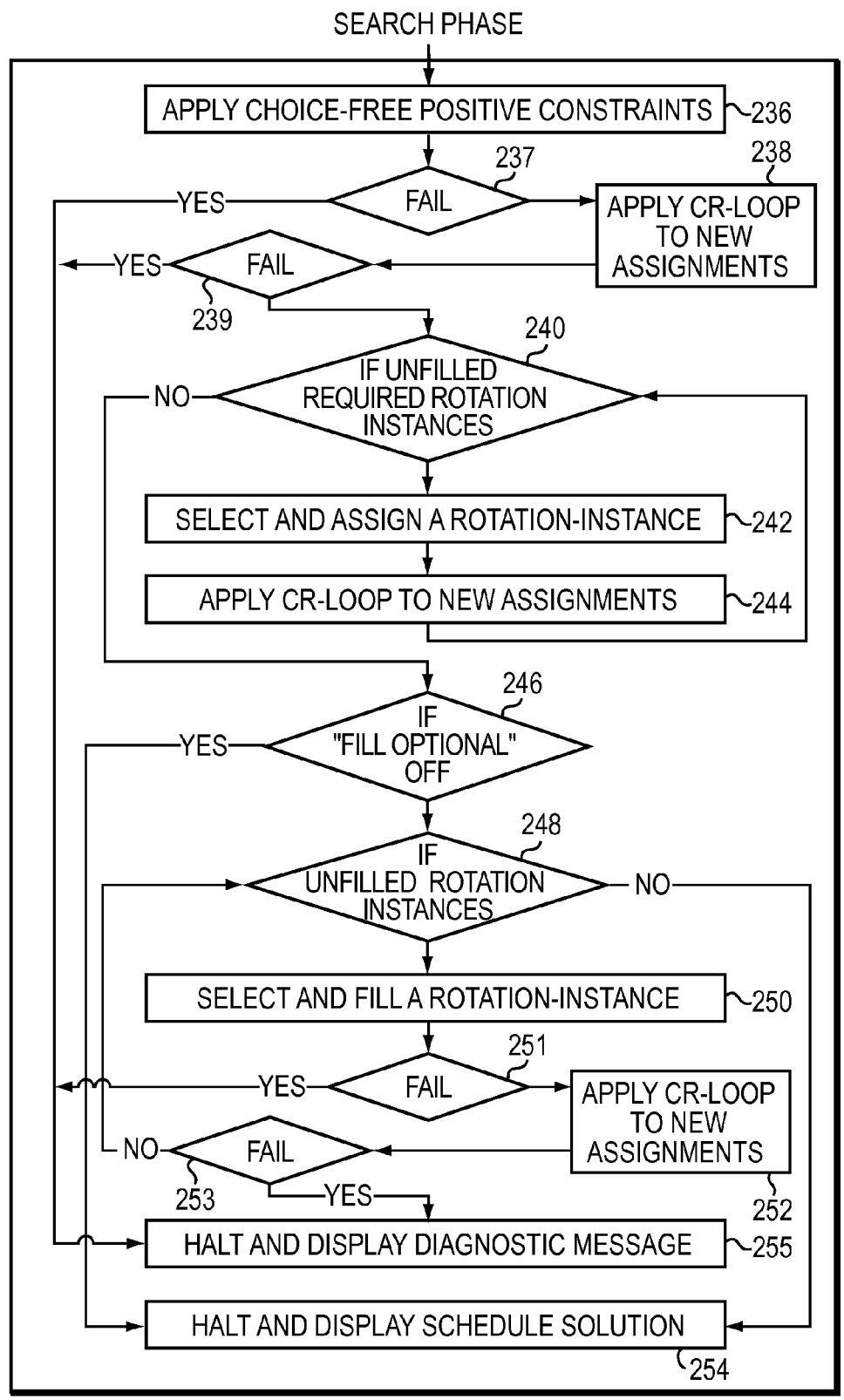

FIGS. 2a and 2b illustrate the automatic scheduling algorithm. The Automatic Scheduling Algorithm proceeds in two phases, 'pre-processing' and 'search.'

Pre-Processing

The pre-processing phase of the automatic scheduling algorithm is a preliminary phase in which data structures that facilitate the search phase of the algorithm are set up, and certain immediately apparent assignments and/or inconsistencies are detected. The assignments made during the pre-processing phase of the algorithm are those assignments that are not the result of any arbitrary choices in making assignments and which, therefore, must be present in any acceptable schedule solution. Because these assignments must be present, no backtracking over assignments is necessary or possible in the pre-processing phase of the algorithm. The pre-processing phase consists of the following steps:

Using the algorithm parameters to calculate the set of slot-instances (steps 212-214). This set consists of one or more slot-instances for each slot in the Slot Class parameter associated with a shift in the Shift Class parameter, for each date between the Start Date parameter and the End Date parameter, and in the calendar parameter, and on which the shift occurs. The number of slot-instances generated by a slot on a date is the maximum value of the multiplicity of that slot over the days in the rotation of the shift containing the slot in which the date occurs.

Calculating and associating to each slot-instance a slot list—the list (step 214) of those employees available throughout the duration of the shift associated with the slot-instance on each date on which the rotation containing the slot-instance occurs, and contained in the class of employees acceptable for assignment to the slot associated with the slot-instance, thereby creating a list of those individuals both available and acceptable for assignment throughout the rotation-instance containing the slot-instance.

For each active constraint and preference, calculating the actual values of Employee Class, Calendar Classes, Shift Classes, and Slot Classes in each active constraint, resulting from the values of the algorithm parameters. This step may discover that some active constraints either have no effect or cannot be satisfied. For instance, if there are no nurses in the employee parameter, the constraint
   'If a nurse works the dayshift, a doctor works the same shift'
      has no effect, because the 'If' part of the constraint can never be satisfied. Such constraints can be eliminated from the list of active constraints.
      Conversely, if there are no doctors in the employee parameter, the constraint is unsatisfiable, because the 'then' clause of the constraint can never be satisfied.
      If any constraints are found to be unsatisfiable, this is reported to the user, with the option of either ending the schedule calculation or continuing the calculation with the unsatisfiable constraints made inactive.

For each Conditional Constraint without an antecedent, with a consequent clause with a 'doesn't work' connective, and without variable parts, removing employees in the Employee Class of the clause from the slot list of every slot-instance within a rotation-instance intersecting the time pattern of the clause.

For example, if a constraint says,
   'Every nurse doesn't work the first week of every month'
      nurses can be removed from the slot list of every slot-instance occurring in the first week of a month, and from the slot list of every slot-instance within a rotation that falls partly within the first week of a month.

If this step produces an empty slot list, the algorithm halts, reports the unfillable slot-instances and offers the user the option of ending the calculation or continuing to fill the other slot-instances After this step, this class of constraints is ignored for the remainder of the scheduling algorithm.

For each slot-instance for which the associated slot list contains a single employee, and for each slot-instance already assigned an individual by the choice of parameter 3 above, designating that employee as assigned to the slot-instance. If any of these assignment designations fails at steps (a) or (b) below, the algorithm halts and reports the failure to the user.

When an employee is assigned to a slot-instance either at this step, or at later steps in the algorithm, the following actions take place:

- a—The employee is immediately assigned throughout the rotation-instance containing the slot-instance, if this is possible. If this is impossible, because the employee is not on the slot list of any slot-instance on one or more days in the rotation-instance containing the slot-instance, the assignment designation fails.
- b—Each Time Limit with a maximum value, with the employee in its Employee Class of Time Limit and with the slot-instance in each of its Calendar Class, Shift Class and Slot Class is checked for violation of the Time Limit maximum. If a maximum value is violated, the assignment fails.
- c—Otherwise, the employee is removed from the slot list of every other slot-instance that temporally overlaps the newly assigned slot-instance, so that no employee is ever assigned to work at 2 jobs or in 2 places at the same time.
- d—The assignment is placed on the list of new assignments.
- e—The slot-instance is removed from the list of unassigned slot-instances.

For each Conditional Constraint without an antecedent, with a consequent clause with a 'works' connective, and without variable parts, assigning every employee in the Employee Class of the clause to slot-instances throughout the time pattern of the clause (step 226).

For example, if a constraint says,
'Every doctor works the doctor slot in the dayshift on every Tuesday in March'
each doctor must be assigned to a slot-instance associated with the doctor slot in the dayshift on each Tuesday in March.
If this is impossible, because of an insufficiency of slot-instances, an employee's limited availability, a Time Limit, or another inconsistency—the algorithm halts and reports this failure, allowing the user to either end the calculation or continue with the unsatisfiable constraints inactivated.

After this step, this class of constraints is ignored for the remainder of the scheduling algorithm.

For each active individual Time Limit with a minimum value, testing whether that minimum value can be satisfied for each employee in the Employee Class of the Time Limit and in the Employee Class parameter. This test is run for every interval of length equal to that of the time interval of the Time Limit and falling within the Start Date and End Date parameters. This test is accomplished by counting the occurrences of an employee on slot lists.

For example, if a Time Limit requires that each nurse works at least 20 shifts a month, but nurse J is on the slot list for only 18 shifts in March, no acceptable schedule will be possible. An analogous test is then run for class Time Limits with minimum values.

If one or more of the Time Limit minima cannot be satisfied, this failure is reported and the user is offered a choice of either ending the schedule calculation or continuing the calculation and ignoring the unsatisfiable Time Limits.

For each of the preceding comparisons between slot list occurrences and Time Limit minima for individual Time Limits, if there is an exact numerical match, designate all the assignments that cause the exact equality. For example, if a Time Limit minimum requires Joe to work at least 20 shifts in March, and Joe is eligible to work exactly 20 shifts in March, then Joe is assigned to those 20 shift.

If this set of assignments cannot be made, the failure is reported to the user.

Reordering each slot list, according to the preferred individual orderings, individual preferences, and optimizations applying to the slot list. This reordering is performed by applying the preference and optimization constraints according to the priority established by the user in his listing of those constraints. Constraints lower on the list cause reordering of a slot list only within classes of employees for which constraints of higher priority are indifferent For example, if there are 2 preferences:
'In the emergency room, prefer doctors with lower salary'
'In the emergency room, prefer doctors with higher seniority'
and the preferences are listed in that order, then the employees on the slot list for an emergency room slot will be ordered with lower salaries first. If two or more doctors have the same salary, those doctors with the same salary will be ordered according to seniority, with more senior doctors first.

Modifying the set of the active Conditional Constraints. This modification takes place in 3 steps—Equality Removal, Double Negation Removal, and Generation of Contrapositives.

Equality Removal

Clauses containing an 'equal' operator are rewritten as a pair of clauses with <= and >=N place of =. So, for example, a clause containing the expression 'N=5'
'Joe works exactly 5 days in April'
is replaced by the pair of clauses containing the expressions 'N<=5' and 'N>=5':
'Joe works 5 or fewer days in April'
'Joe works 5 or more days in April.'

Double Negation Removal (Step 212)

Clauses in all active constraints are rewritten to remove double negations. A clause can be made negative in several ways—either by choosing 'doesn't work' as the connective, or by an occurrence of a 'less than' or 'less than or equal' numerical operator within the clause. Thus,
'Joe doesn't work the dayshift in April'
and
'Joe works less than 30 hours in April'
are both negative clauses. However, the clause
'Fewer than 3 doctors each work less than 5 dayshifts in April'
has two 'less than' operators, and so is doubly negated. If there were 8 doctors and 12 dayshifts in April, this clause could be rewritten as
'Five or more doctors each work 7 or more dayshifts in April.'

The algorithm replaces the original doubly negated clause with this positive equivalent. Where there are more than two negations in a clause, the same procedure is repeatedly used to replace it with an equivalent clause with either no negations or one negation.

These rewritten constraints, with extra negations removed from their clauses, are not visible to the user of the program.

Contrapositive Generation (Step 214)

The algorithm next enlarges the set of active Conditional Constraints. For each active Conditional Constraint with a non-empty antecedent, the algorithm calculates a set of new constraints, called the 'contrapositive' of the original constraint, and adds these new constraints to the list of active constraints. Each set of contrapositive constraints is logically equivalent to the constraint it is derived from and, therefore, imposes no further restriction on acceptable schedule solutions. However adding contrapositive constraints speeds up the search procedure by causing early pruning of branches of the search tree that cannot lead to scheduling solutions. Contrapositive constraints are not visible to the user of the program.

For a constraint of the form
'If clause 1 then clause 2'
the set of contrapositive constraints is the single constraint
'If not clause 2 then not clause 1.'
For example, the contrapositive of the constraint
'If Joe works any Tuesday, then Al works the next day.'
is the constraint
'If Al doesn't work any Wednesday, then Joe doesn't work the day before'

Obviously, any schedule solution which satisfies the first of these constraints also satisfies the second, and vice versa, so adding the contrapositive to the list of active constraints does not eliminate any candidate schedule solutions. However, the effect of the contrapositive constraint is to cause Joe to be removed from the candidates for assignment to the slot-instances on a Tuesday as soon as Al has been assigned to a slot-instance on the next day. The prompt removal of these potential assignments, which would ultimately lead to failure if they were tried, speeds up the search procedure.

A constraint with N antecedent clauses generates a set of N contrapositive constraints:
For a constraint of the form
'If clause 1 and clause 2 . . . and clause n then A'
the contrapositive is the set of n constraints
'If clause 1 and clause 2 . . . and clause (n−1) and not A then not clause n.'
'If clause 1 and clause 2 and . . . clause (n−2) and clause n and not A then not clause(n−1)'
.
.
.
'If clause 2 and . . . clause n and not A then not clause 1.'
Each of the constraints in the contrapositive is constructed by negating the consequent clause A and moving it to the antecedent. The clauses of the antecedent are successively negated and moved to the consequent.
For Unconditional Constraints, i.e., constraints with no antecedent and a consequent clause A, the contrapositive is
'If not A then Failure'
This is an instruction to the search algorithm that whenever clause A cannot be satisfied by a partial schedule solution, the search must backtrack.

In the above description of contrapositives, 'Not C' stands for a new clause derived from clause C. 'Not C' is constructed so that it is the logical negation of C, in the sense that 'Not C' is satisfied by exactly those complete schedule solutions that do not satisfy C. In general, 'Not C' is constructed from C by modifying the Employee Pattern:

If the Employee Pattern in C requires that N or more employees individually work a pattern of assignments, the Employee Pattern in Not C will require that fewer than N employees work the same pattern of assignments. In case the Employee Pattern requires that between N and P employees, with P>N, individually work some pattern of assignments, Not C will be expressed by two clauses, one requiring that more than P employees work the pattern, and one requiring that fewer than N employees work the pattern. 'Not C' is satisfied if either of these two clauses are satisfied. The two clauses generate two distinct contrapositives, with one of the two clauses standing in place of 'Not C' in each of the two contrapositives.

If the Employee Pattern in C requires that N total employees work some pattern of assignments, the Employee Pattern in Not C and a modified Duration Specifier in Not C will require that fewer than N employees work at some point in the same time and shift pattern.

If the Employee Pattern in C requires that N employees as a group work a pattern of assignments, Not C will state that no N employees as a group work that pattern.

Not all Unconditional Constraints are used to generate contrapositives, since the Unconditional Constraints without variable part are used and removed at an earlier pre-processing step. An Unconditional Constraint generates a contrapositive only if its consequent clause contains a variable part. For example, the unconditional negative constraint 'no doctor works the night shift' has no variable part. But 'some doctor does not work the night shift' does have a variable part. It is satisfied by choosing a doctor—who will not work the night shift—from among the set of doctors. Similarly, satisfying 'Joe works the morning shift some day in January' requires choosing from among the days in January.

The Search Phase (Steps 218-255)

If, at the end of the pre-processing phase, there are either unfilled required slot-instances, unsatisfied Time Limit minima, or unfilled optional slot-instances within the 'fill optional slot' parameter class, the algorithm moves to the search phase to complete the schedule. During the search phase, repeated choices of employees and slot-instances are made in order to generate new assignments. Because these choices are, in general, underdetermined by the available data, arbitrary choices must be made at some points in the search procedure.

Choices are required at 2 points in the algorithm:
1—When all the consequences of the current assignments have been calculated, but the schedule is still not complete
2—In order to satisfy a constraint
For example, to satisfy the constraint
'at least one doctor works on Tuesday March 24'
a doctor must be selected.
To satisfy the constraint
'Joe works some day in March'
a slot-instance in March must be selected.

After making one or more assignments, the algorithm may discover that a contradiction has been reached and that no acceptable scheduling solution containing the current assignments is possible. In this case, the algorithm must backtrack, removing one or more of the current assignments and trying a different employee or slot-instance. In one embodiment of the program, this backtracking takes place by replacing the most recently made assignment (chronological backtracking). In other embodiments of the program, the assignment to be replaced is determined in another way, for example, by replacing the assignment that led to the largest number of contradictions, or that caused the largest number of employees to be deleted from a slot list that ultimately became empty (dependency based backtracking).

If the algorithm needs to backtrack from an assignment but no such further backtracking is possible (because all 'earlier' rotation-instances are unfillable) the algorithm adds the rotation-instance under consideration to the list of unfillable rotation-instances and removes it from the list of unassigned rotation-instances. The algorithm then selects another unassigned rotation-instance to fill.

Whenever any assignment is made during the processing phase, that assignment is placed on a list of new assignments and this list of new assignments is checked against the active Time Limits, Conditional Constraints, and Regularity Constraints to see what further facts about acceptable schedules can be drawn from the presence of the new assignments. This checking process may itself produce new assignments and these further assignments are themselves checked against the active Time Limits, Conditional Constraints and Regularity Constraints. This subroutine (constraint propagation) continues until no further assignments are generated.

The processing phase of the scheduling algorithm comprises five steps:

1—Drawing further consequences from the assignments made during the pre-processing phase. This step comprises two substeps:

a—Applying the CP loop (step 226) with all assignments made thus far as the set of new assignments b—For each of comparison between slot list occurrences and Time Limit minima for group Time Limits, if there is an exact numerical match, find an assignment of the employees in the Employee Class of the Time Limit that exactly meets the Time Limit if such a matching occurs. Determining whether such matches exist and generating such matches if they do exist is accomplished by a 'marriage algorithm' well known to those skilled in the art.

For example, if a Time Limit requires that

'the nurses (as a group) work at least 200 hours in each week' and there are exactly 200 hours of slot-instances for nurses in the week of January 10-17, then the marriage algorithm will be used to assign a nurse to each of those slot-instances if such an assignment is possible.

Since more than one such group of assignments may be possible, the scheduling algorithm may backtrack to this group of assignments and replace it with another group of assignments that meets the Time Limit 2—Making assignments as needed to satisfy any Unconditional Constraints with variable parts (steps 226-238).

For example, if the unconditional positive constraint

'Joe works some day in each month' is not yet satisfied for one or more months, a slot-instance will have to be selected to assign Joe to in each of these months. The CR loop is run after each of these assignments. Since a choice is involved, the algorithm may backtrack over these selections if it later reaches a contradiction.

Similarly, if the unconditional negative constraint

'Joe does not work some day in each month' is not yet satisfied (satisfaction for negative clauses is explained below), a day will have to be selected in each of some months, and Joe removed from the slot lists of every slot-instance occurring on that day, so as to prevent Joe from working on that day.

3—Repeatedly selecting (step 242) a rotation-instance and assigning an eligible employee to that rotation-instance. This set of assignments, and every assignment made during the processing phase, is first checked for violation of a Time Limit maximum. If such a violation is found, the assignment fails and backtracking takes place. Next, the CR-loop is run with these new assignments as input. If the CR loop fails, backtracking takes place. This process is repeated until either every required slot-instance has either been assigned an employee or found to be unfillable.

This procedure requires repeatedly choosing an unfilled rotation-instance. In one embodiment of the invention, the unassigned rotation-instance with the smallest number of eligible employees is chosen, with ties among rotation-instances being broken in chronological order.

This procedure also requires repeatedly choosing an employee from among the eligible employees for a rotation-instance. In one embodiment of the invention, the employee chosen is that employee who has not yet been tried for assignment to the rotation-instance, and who is in first place on the largest number of the slot-lists of the slot-instances comprising the rotation-instance. Ties among employees are broken by looking at successively lower places on the slot-lists. In other embodiments of the program other criteria for the selection of employees may be substituted or combined with this method of ranking. These other criteria may include the total number of assignments for an employee thus far and the proximity to meeting or violating various Time Limits for individuals.

4—If there are still Time Limits with a violated minimum value, repeatedly selecting unfilled rotation-instances (steps 248, 250) that increase the number of assignments that count for one or more of these Time Limits, assigning an eligible employee to the rotation-instance, applying the CR loop with these assignments as input, and backtracking if the CR loop fails, until either no such Time Limits remain or no such unfilled rotation-instances remain.

5—If there are still Time Limits with violated minimum values after this step, these violations are reported to the user when the schedule is displayed. If there are still unfilled optional slot-instances within the 'fill optional slot' class parameter, repeatedly selecting unfilled optional rotation-instances containing such an unfilled slot-instance, assigning an eligible employee to the rotation instance,' and applying the CR loop with these assignments as input, until no unfilled optional slot-instances within the 'fill optional slot' class parameter remain. In one embodiment of the program, this sequence of assignments is made without backtracking—if an assignment causes an inconsistency, the slot-instance of that assignment is simply left unfilled.

When the processing phase is completed, algorithm halts and a display screen shows the employee assignments for all assigned slot-instances and the unassigned slot-instances, if any.

CR-Loop

In carrying out the above steps, the algorithm repeatedly calls a subroutine called the 'Constraint and Regularity Loop (CR-Loop) (244).'

Figure 3:
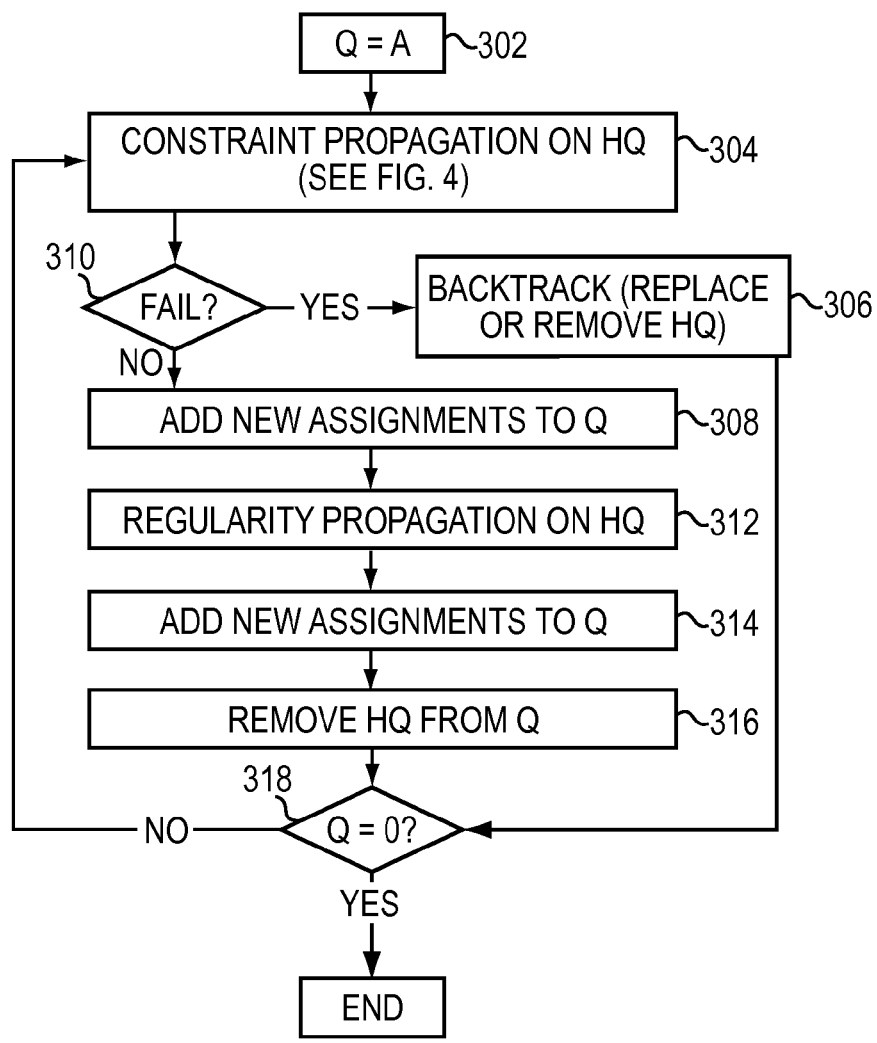
FIG. 3 and FIG. 4 are flow charts of a constraint propagation subroutine.

The Constraint and Regularity Loop subroutine is illustrated in FIG. 3.

When passed a list of new assignments as input (step 302), this list becomes the initial value of an internal queue maintained by the CR-Loop. The CR-Loop tests each of the assignments on the queue against all the Conditional Constraints (by calling the 'Constraint Propagation' subroutine 304), and then tests each input assignment against all the Regularity Constraints (by calling the 'Regularity Propagation' subroutine 312). Each of these two subroutines may generate new assignments, which are added to the end of the queue (steps 308,314). The CR-Loop processes the assignments on the queue until it is empty (step 318).

The Constraint Propagation subroutine (described in more detail below) compares a single input assignment with the active Conditional Constraints, and makes all possible inferences based on the constraints and the input assignment, detecting constraint violations, and possibly making new assignments or removing employees from slot lists. Whenever new assignments are produced, they are added to the queue of the CR-loop (steps 308, 314).

The Regularity Propagation subroutine 312 compares its input assignment with all active Regularity Constraints. Whenever a Regularity Constraint applies to the input assignment, the employee in the input assignment is assigned to every unfilled rotation-instance specified by the Regularity Preference, for which the employee is eligible and which does not violate a Time Limit maximum. These new assignments are placed on the queue of assignments for the CR-Loop.

Constraint Propagation

Figure 4:
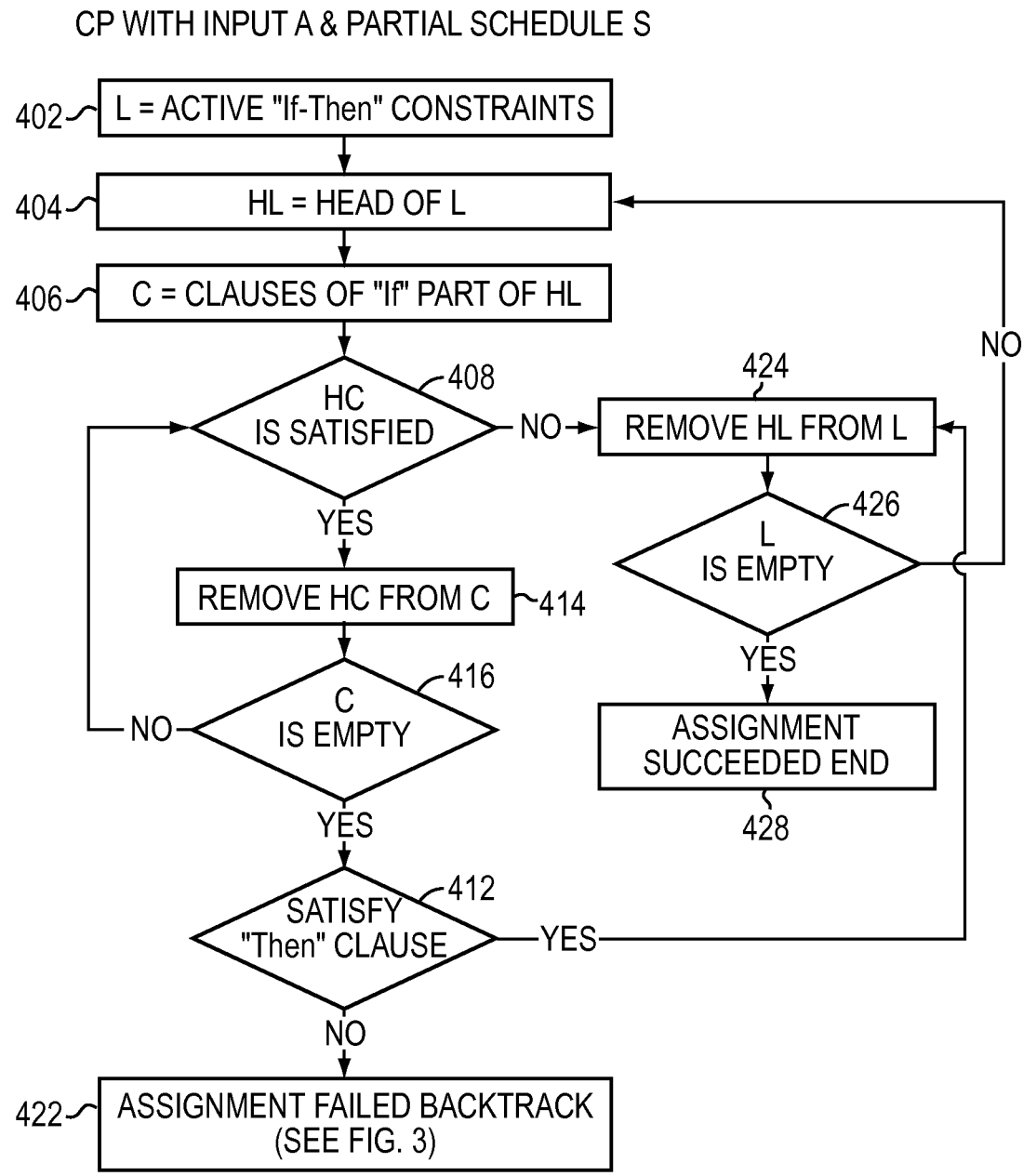

The Constraint Propagation subroutine is illustrated in FIG. 4.

Constraint Propagation is a subroutine of the CR-Loop. Whenever one or more employees are assigned, the algorithm repeatedly calls the Constraint Propagation subroutine 304, successively passing it each of the new assignments.

The Constraint Propagation subroutine 304 compares its input assignment with the antecedent clauses of each Conditional Constraint in every possible way (steps 406-428). Whenever all the antecedent clauses in an Conditional Constraint are satisfied by an instantiation of the variable parts of the antecedent clauses that involves the new assignment in some way, action is taken to satisfy the consequent part of the constraint, if possible.

If, in this process, a Conditional Constraint either cannot be satisfied or leads to an immediate contradiction, that constraint fails (steps 422). If a strong Conditional Constraint fails, the constraint propagation subroutine fails and the input assignment is withdrawn, as are any already calculated consequences of the input assignment. If a weak Conditional Constraint fails, the immediate effects of that constraint are withdrawn, but the input assignment is not withdrawn.

Constraints with a positive 'then' clause are violated when the 'If' part of the constraint is satisfied, but no assignment can satisfy the 'Then' part of the constraint (step 422). For example, if the input assignment assigns Joe to a slot-instance on a Tuesday, the Conditional Constraint 'If Joe works on a Tuesday, then Al works the same day'
will fail if there is no unassigned slot for which Al is eligible, occurring on the same day as the input assignment.

If such a constraint does not fail, it causes a new assignment. For example, if the input assignment assigns Joe to a slot-instance on a Tuesday, the above Conditional Constraint will cause a new assignment, assigning Al to a slot-instance on the same day as the input assignment.

If new assignments are made, they are immediately extended and checked according to the procedure at step 5 of the pre-processing phase. If these steps fail, the constraint that caused the assignments fails. Otherwise, the new assignments are placed on the queue of assignments for the CR-Loop.

Employees are removed from slot lists by constraints with negative 'then' clauses. For instance, if the input assignment assigns Joe to a slot-instance on a Tuesday, the Conditional Constraint 'If Joe works on a Tuesday, then Al doesn't work the same day'
will cause 'Al' to be removed from the slot list of eligible employees for all slot-instances occurring on the same day as the input assignment.

If employees are removed from slot lists, and any slot list becomes empty, the constraint that caused the slot list to become empty fails. Also, if employees are removed from slot lists, Time Limits involving these slot lists are checked to see if any Time Limit minima become unsatisfiable, and for minimum exact matches. If one or more minima become unsatisfiable, the constraint that caused this fails. If the slot list of a slot-instance contains only one employee as a result of removing employees from that slot list, the remaining employee is assigned to that slot-instance, and that assignment is checked and placed on the queue. If an exact match is detected between a Time Limit minimum and the resources necessary to satisfy that minimum, assignments satisfying the exact match are made, if possible, and placed on the queue. If no such assignments are possible, the constraint causing the exact match fails.

The description of Constraint Propagation given above depends on the notion of a clause being satisfied by a partial schedule. How a clause is satisfied depends on whether the clause is positive or negative.

Satisfaction for positive clauses is straightforward. A partial schedule P satisfies a positive antecedent clause, C, for a given instantiation of the variable terms in C, if C is true in P with these instantiations.

For example, the clause

'Joe works two or more days in the week of march 10 to march 17'
is true in a partial schedule P only if P contains assignments of Joe occurring on two or more days in the week of march 10 to march 17. And the truth of the clause 'Some employee works two or more days in some week'
in a partial schedule P will depend on the instantiations of the variable parts 'some employee' and 'some week.' For each employee and each week, it will be satisfied or not depending on whether or not that employee works at least 2 days in that week.

Similarly, if either of these two clauses occurs as the consequent clause in a constraint, the algorithm adds assignments to P in order to satisfy the clause using the same criteria, e.g., if Joe is not already working 2 or more days in the week of March 10 to March 17, the algorithm creates extra assignments to make sure that Joe does work at least 2 days in the week.

Satisfaction of negative clauses by partial schedules is more subtle. Simply to say that a negative clause is satisfied by a partial schedule P if the condition expressed by the clause is true in P would not work. For example, the negative clause 'Joe doesn't work in February'
is, in some sense, satisfied by the empty partial solution E in which no assignments at all have been made, because, since E contains no assignments, E contains no assignments of Joe to slot-instances in February. However, as assignments are added to E by the scheduling algorithm, Joe may later be assigned to work in February, thereby violating the clause. Therefore, the proper interpretation of satisfaction for a negative clause C by a partial schedule P is to say that C is satisfied by P if every complete schedule extending P satisfies C. However, this version of satisfaction is too difficult to calculate—it requires knowledge of all the complete schedules extending a partial schedule, while the task at hand is just to calculate one or more of those schedules.

In the actual program, this hard to calculate criterion for satisfaction is replaced by a simpler one—a negative clause is satisfied by a partial schedule P when it can be shown in some immediate and easily calculated way that the clause must be true in every schedule extending P. In one embodiment of the program, this is done by counting available resources. So for example, the negative clause C 'Joe works less than 4 days in March' will obviously be satisfied by any extension of a partial schedule P, if the total number of days in March on which Joe is already assigned by P or for which Joe is eligible in P is less than 4. In other embodiments of the program, deciding the satisfaction of negative clauses may also involve checking potential assignments against Time Limit maxima. For example, if there were 5 days in March during which Joe was eligible to work, but 4 of these days were Tuesdays, and there was also a Time Limit 'All employees work fewer than 3 Tuesdays in every month' then C would also be satisfied; Joe can only work at most 2 Tuesdays plus the one non-Tuesday for which he is eligible, so he can work at most 3 days in March.

Similarly, if a negative clause occurs in the consequent of a constraint, the same satisfaction criterion is used by the algorithm to make sure that the clause is satisfied. For example, to satisfy 'Joe works less than 4 days in March' a choice of 3 days in March must be made, and Joe must be removed from the slot list of all slot-instances occurring in March, except those occurring on the 4 chosen days.

If, as in this example, the satisfaction of a negative 'Then' clause involves making choices among employees or time periods, the number of such choices is restricted by the search depth parameter, and these choices may be revisited by backtracking.

To test the Conditional Constraints against a new assignment in every possible way, each antecedent clause in each active Conditional Constraint is successively tested against the new assignment (steps 416-428).

If a clause is positive, the assignment is examined to see whether the assigned employee and slot-instance fall within the Employee Pattern and time pattern of the clause respectively. If they do, any interpretations of the variable parts in the clause that are made in matching the assignment to the clause are carried over to the other clauses in the antecedent of the constraint. Then, if all the antecedent clauses can be satisfied, action is taken to satisfy the consequent of the constraint.

For example, suppose the assignment is of Joe, a doctor, to a slot-instance on Tuesday, March 25. In the constraint 'If a nurse works the morning shift on any day, and a doctor works the next day then the same nurse doesn't work in the next month' the assignment doesn't match the first clause—since the Employee Pattern of that clause includes only nurses and not doctors, but it does match the second clause. In making that match, the variable part 'a doctor' gets instantiated by 'Joe' and the variable part 'next day' gets instantiated by 'Tuesday, March 25.' These instantiations get carried back to the first clause so that 'any day' gets instantiated by 'Monday, March 24.' The variable part 'a nurse' remains uninstantiated, and so will be checked against all nurses. Whenever a nurse is found who works on March 24, both clauses of the antecedent will be satisfied and the consequent clause, a negative clause, will have to be made true by removing that nurse from the slot lists of all slot-instances in the next month, April.

If a clause is negative, all interpretations of the variable parts of the clause which make the corresponding positive clause impossible to satisfy are listed. Each of these interpretations is tested with the new assignment missing. Only those interpretations which make the clause impossible to satisfy with the new assignment included but not with the new assignment excluded are kept. Each of these interpretations is then carried to the other antecedent clauses, and then to the consequent clause.

For example, if the assignment is as above, in the constraint

'If a nurse works the morning shift on any day, and no doctor works the next day then the same nurse doesn't work in the next month' there may be 15 days for which the second clause is satisfied, e.g., because there is no doctor who is eligible to work on those days. Prior to the current assignment, there may have been only 13 such days. That is, Joe was eligible to work on 2 of the 15 days, but once he received the present assignment he became ineligible to work on 2 of those days because of a negative Conditional Constraint or a Time Limit triggered by the assignment. If so, the algorithm will use just those 2 days to instantiate the variable 'next day' in the second clause, and then carry that instantiation throughout the constraint as in the prior example.

After all Conditional Constraints and Time Limits have been tested against the input assignment, new assignments may have been made. If so, the Constraint Propagation subroutine places these new assignments on the queue of the CR-loop and then terminates.

Scheduling Diagnosis Functions

Whenever the automatic scheduling algorithm cannot completely solve a scheduling problem, the user has access to several diagnostic tools that help him find the cause of the scheduling failure.

On any schedule display format, the user can highlight any slot-instance or rotation-instance and view the associated slot-list of employees. After use of the automatic scheduling algorithm, the slot-list will be annotated to show which employees were tried in filling the slot, and why each of these tried employees were unable to fill the slot. If the slot-instance was assigned, the reason for the assignment—manual entry, assignment already in schedule, Time Limit, Regularity Constraint, Conditional Constraint, etc., will also be shown. In the case of Conditional Constraints and Regularity Constraints, the assignments that triggered the constraint will also be viewable.

For each Time Limit, the user can view a list of all employees who have reached a maximum value of the Time Limit and where in the schedule each maximum was reached. The user can also view all those employees who cannot reach a minimum value of the Time Limit and where the failure to reach the minimum occurred.

Any schedule display format can be filtered to show only unfillable slot-instances. The user can also view filled-slot-instances with either a numerical count or graphical representation of the number of trial assignments that were made before the slot was filled. Slot-instances or rotation-instances that required many trial assignments represent potential 'bottlenecks' in the scheduling problem that the user may need to modify in order to completely solve a scheduling problem.

For each active constraint, the user can view a count of the number of times that constraint caused backtracking, and a graphic display of the slot-instances where a given constraint caused backtracking Constraints that cause frequent backtracking are most likely to be responsible for scheduling failures, and may need to be modified or made inactive in order to completely solve a scheduling problem.

Whenever a partial or complete schedule is displayed, the user has access to a display of all the input parameters of the Automatic Scheduling Algorithm that gave rise to that schedule.

Schedule Displays

Schedules and partial schedules can be displayed and modified using several formats—Grids, Lists, and Employee Calendar Displays. Each of these display formats supports a common set of features:

1—Each display format is filterable by entering an Employee Class, a Calendar Class, a Shift Class, a Slot Class, and a Start and End Date. Only assignments for employees in the Employee Class to slots within the Slot Class associated with shifts within the Shift Class and occurring on a day within the Calendar Class between the Start and End Dates dare displayed. The default values for all the above classes is 'all' and the default values for the Start and End Dates for the display are the Start and End Dates of the schedule being displayed.

2—Each display format graphically shows the locked/unlocked status of each assignment and supports switching the locked/unlocked status of individual assignments and classes of assignments 3—Each display format supports the means for manual modification of assignments, and for viewing the inconsistencies generated by candidate manual assignments 4—Each display format is available in a modified form in the Attendance Mode of the program. In this modified form, the display shows both scheduled and actual attendance and supports entry of attendance and substitution for employees Grids Grids show assignments in a rectangular array. There are two grid formats:

In the first Grid format, rows are labeled by employee names and columns by dates in the schedule. Within each cell of the array is a description of the corresponding employee's assignments for that date.

In the second Grid format, rows are labeled by shifts (and slots) and columns by dates in the schedule. Within each cell of the array is a description of the employee assignments for the given shifts and slots for that date.

Lists

Assignments can also be displayed in list format. Assignments can be listed either by day or by rotation. If assignments are listed by day, the days within the schedule interval are listed chronologically. For each day, all the assignments are displayed, showing the assigned employee, the shift, the slot, the starting and ending times, and the total number of hours worked.

If assignments are listed by rotation, assigned rotations are listed chronologically by starting date. Each rotation assignment display shows the assigned employee, the shift, the slot, the starting date and ending date of the rotation, the daily hours, the days comprising the rotation and the total number of hours and days in the rotation.

Employee Calendar Displays

Employee Calendar Displays show the schedule for a single employee or specified Employee Class in a format resembling a traditional wall calendar, and are suitable for printing and distribution to employees. The dates in the schedule range are graphically displayed in a monthly calendar format. Time intervals during which the selected employee or employees work are shown as colorable horizontal bands and are labeled with the shift and slot assignment. Statistical summaries of the number of days and hours worked per week are shown at the right side of the display.

Statistics

There are two statistics display screens—'Group Statistics' and 'Individual Statistics.' The statistics screens display statistical summaries of any partial or complete schedule solution. The statistics screens can be configured and printed so as to produce standard reports.

Statistics are displayed in a rectangular array. In the 'Group Statistics' screen, each row of the array is labeled by an Absolute Employee Class Specifier chosen by the user. Each column is labeled by Shift Class, Slot Class, and Calendar Class specifiers chosen by the user. Each cell of the array displays the amount of time worked by all members of the corresponding Employee Class during the corresponding Shift, Slot and Calendar Classes. Time can be displayed in units of minutes, hours, days, shifts, or rotations.

The total time for each Employee Class summed over all the specified classes is listed at the far right of each row and the total time for each Shift, Slot and Calendar Class summed over the specified Employee Class is shown at the bottom of each column. If any employees or shifts are listed in more than one class, the totals are adjusted so as to avoid counting a shift or employee twice.

The accumulated values for cumulative numerical attributes summed over rows and columns can also be viewed at the right hand side of the rows or the bottom of the columns.

In the 'Individual Statistics' screen, rows are labeled by individual employees and columns by Shift Class, Slot Class and Calendar Class. Each cell of the array displays the amount of time worked by the corresponding employee within the corresponding Shift Class, Slot Class and Calendar Class.

A modified form of the statistics screens, showing scheduled statistics vs. the statistics of actual attendance, absences and substitutions is available in the Attendance Mode of the program (below). The entries for attendance, absence and substitution are further filterable by attribute ranges for the attributes attached to attendance, absences and substitutions.

Attendance

The program has an additional operational state, the 'Attendance Mode.'

In the Attendance Mode the user is able to keep track of the actual attendance of his employees. The Attendance Mode becomes available once a user has generated and 'accepted' a schedule. This schedule is fixed and archived and is used as the basis to track the expected attendance.

In Attendance Mode, the user can record whether or not an employee is present for his scheduled assignments and, if present, enter the actual times that the employee starts and ends work. The program records and archives this actual attendance, displays it and calculates statistics based on it.

When an employee has either been declared absent for an assignment, marked late for an assignment, or if no assignment for a slot-instance has been made by the time the assignment begins, the program prompts the user for a substitute employee to fill the unfilled slot-instance and provides lists of available and qualified substitute employees so that the user may manually fill the slot-instance. Alternatively, the user may allow the scheduling algorithm to make one or more substitute assignments as necessary. In this case, the algorithm uses the actual attendance up to the present and the scheduled attendance from the present forward as a partial schedule to complete. Since actual attendance has already occurred, the algorithm will not backtrack over actual attendance.

If an employee's attributes include communication information such as a phone number, pager number, E-mail and/or social media address, the program allows the user to automatically notify substitute employees of their new assignments.

The attendance statistics can be transferred to payroll, human resource management, personnel management or enterprise management software. In general any of the data or library entries can be exchanged between the system and other software databases, libraries and programs using the system's import and export features. The system can also be configured to take advantage of the information sharing capabilities of the internet.

While this invention has been particularly shown and described with references to preferred embodiments thereof, it will be understood by those skilled in the art that various changes in form and details may be made therein without departing from the scope of the invention encompassed by the appended claims.

What is claimed is:

1. A computer apparatus for implementing a resource scheduling system comprising:
a memory structured to enable accessing stored scheduling parameters for optimized scheduling of resources, the scheduling parameters including:
a set of resources, each resource having any number of associated user-defined attributes,
at least one calendar having a user-specified plurality of temporal intervals representing a pattern of user-specified dates, for utilizing resources,
at least one shift, each shift including a user defined pattern of time periods representing a recurring pattern of time periods for resource utilization,
at least one slot representing resource demand, resource demand being demand for one or more individual resources of the set of resources during at least one user selected shift of the at least one shifts, and
a set of natural language resource constraints of the resources in the set based on the at least one resource and the at least one slot, the natural language resource constraints generated by a user;
an automatic calendar generator configured to create a calendar for resource scheduling based on the at least one calendar in memory;
a resource manager configured to select a shift from the at least one shift in memory, the resource manager further configured to allocate the selected shift to a time interval of the created calendar, the shift comprising slots representing resource demand for the time interval of the created calendar;
a scheduling processor configured to assign resources from the set of resources in the memory to the shift slots by accessing the memory to apply the set of natural language resource constraints to: (i) attributes of each resource of the set of resources and (ii) attributes of the shift, to determine the resources that optimally fulfill the respective resource demands of each shift slot, the applying of the set of natural language resource constraints include:
(a) eliminating the natural language resource constraints that have no effect on the assigning and assigning resources to the shift slots based on remaining natural language resource constraints, and
(b) automatically modifying the remaining natural language resource constraints based on attributes of the set of resources and attributes of the shift, such that applying the modified resource constraints optimize the assigning of the resources to the shift slots;
wherein the scheduling processor is further configured to:
schedule simultaneously multiple resources of the set of resources, such that the simultaneously scheduled multiple resources fulfill resource demand represented by the shift slots; and
for one resource of the set of resources, allow generation of one schedule of different shifts of one resource for different slots of demand of the one resource; and
a user interface configured to present a graphical user interface as a display and enable the user to define at least one attribute of the stored scheduling parameters with objects, including employees, resources, calendars, shift slots, assignments, and replacements by presenting a range of choices for type of each attribute, the choices being at least one of a defined list of alpha-numeric strings, numeric values having defined numerical limits, or a Boolean operator, and to generate the natural language resource constraints.

2. The computer apparatus of claim 1, wherein the scheduling processor assigns individual resources to instances of demand for resources represented by the at least one slot and the one or more user-defined shifts.

3. The computer apparatus of claim 1, further comprising: any number of constraints.

4. The computer apparatus of claim 1, wherein the user interface presents a range of choices for each of the at least one additional constraint.

5. The computer apparatus of claim 1, wherein at least one resource of the set of resources has an associated set of time intervals during which the at least one resource is available to be scheduled.

6. The computer apparatus of claim 1, wherein the at least one or more individual resources, the at least one calendar, and the at least one slot are represented as objects.

7. The computer apparatus of claim 6, wherein each object is capable of being switched between active and inactive status.

8. The computer apparatus of claim 6, wherein at least one attribute associated with at least one object is of a numeric type and wherein the scheduling processor calculates accumulated totals of the at least one attribute in a schedule involving the at least one object.

9. The computer apparatus of claim 6, further comprising: a user interface for creating and specifying objects.

10. The computer apparatus of claim 1, wherein the scheduling processor assigns individual resources to instances of demand for resources represented by the at least one slot.

11. The computer apparatus of claim 1, wherein the scheduling processor generates diagnostic information.

12. The computer apparatus of claim 11, wherein the diagnostic information comprises at least one of the following: information about conflicts between resource demands, information about resource shortages, information about unavailability of a schedule that satisfies all the resource constraints.

13. The computer apparatus of claim 11, wherein the diagnostic information comprises at least one of the following: information about utilization of the set of resources, information about patterns of demand, and information about resource availability.

14. The computer apparatus of claim 1, further comprising: a user interface for editing the at least one calendar.

15. The computer apparatus of claim 1,
wherein the automatic calendar generator generates a new calendar based on the at least one calendar.

16. The computer apparatus of claim 1, further comprising:
a user interface for graphically displaying a match between the at least one slot representing demand for one or more individual resources and availability of the set of resources, using a rectangular array to display time intervals divided among a plurality of classes.

17. The computer apparatus of claim 1, further including a plurality of classes, the plurality of classes comprising one or more of the following classes: time intervals for which the resource is both available and in demand, time intervals for which said resource is available and not in demand, and time intervals for which the resource is neither available nor in demand.

18. The computer apparatus of claim 1, wherein at least one constraint in the set of resource constraints is an optimization constraint.

19. The computer apparatus of claim 1, wherein at least one constraint in the set of resource constraints is a conditional constraint.

20. The computer apparatus of claim 1, wherein the scheduling processor modifies the set of resource constraints by: (i) replacing each doubly negated clause with a logically equivalent positive clause, and (ii) adding to the set of resource constraints one or more logically equivalent contrapositive constraints for each conditional constraint.

21. The computer apparatus of claim 20, wherein the scheduling processor uses constraint propagation for generating the schedule of resources of the set of resources assigned to demands for resources.

22. The computer apparatus of claim 21, wherein the scheduling processor generates a list of requirement slots and assigns resources to as many as possible of the requirement slots.

23. The computer apparatus of claim 1, wherein the scheduling processor generates a partial schedule satisfying a subset of the resource constraints.

24. The computer apparatus of claim 1, further comprising:
a user interface for designating a generated schedule as accepted and generating a permanent record of the generated schedule.

25. The computer apparatus of claim 1, wherein the resource manager is an employer.

26. A computer-implemented method for resource utilization scheduling, said method comprising:
in at least one hardware processor:
recording, in a memory structured to enable accessing stored scheduling parameters for optimized scheduling of resources, the scheduling parameters including: (i) information about a set of resources, each resource having associated user-defined attributes, (ii) at least one shift, each shift including a user defined pattern of time periods representing a recurring pattern of time periods for resource utilization, (iii) at least one slot associated with each shift representing resource demand, resource demand being demand for one or more individual resources of the set of resources during the associated shift, and (iv) any number of natural language resource constraints of the resources in the set based on the resource demand represented by the at least one slot, the natural language resource constraints generated by the user;
storing in the memory at least one calendar having a user-defined plurality of temporal intervals representing a pattern of user-specified dates for utilizing resources in the set of resources;
creating a calendar for resource scheduling based on the at least one calendar in memory;
selecting a shift from the at least one shift in memory, wherein allocating the selected shift to a time interval of the created calendar, the shift comprising slots representing resource demand for the time interval of the created calendar;
generating a schedule by assigning resources from the set of resources in the memory to the shift slots by accessing the memory to apply the set of natural language resource constraints to: (i) attributes of each resource of the set of resources and (ii) attributes of the shift, to determine the resources that optimally fulfill the respective resource demands of each shift slot, the applying of the set of natural language resource constraints include:
(a) eliminating the natural language resource constraints that have no effect on the assigning and assigning resources to the shift slots based on remaining natural language resource constraints, and
(b) automatically modifying the remaining natural language resource constraints based on attributes of the set of resources and attributes of the shift, such that applying the modified resource constraints optimize the assigning of the resources to the shift slots;
wherein generating the schedule:
schedules simultaneously multiple resources of the set of resources, such that the simultaneously scheduled multiple resources fulfill resource demand represented by the shift slots; and
providing a graphical user interface as a display and enabling the user to define at least one attribute of the stored scheduling parameters with objects, including employees, resources, calendars, shift slots, assignments, and replacements by presenting a range of choices for type of each attribute, the choices being at least one of a defined list of alpha-numeric strings, numeric values having defined numerical limits, or a Boolean operator, and to generate the natural language resource constraints.

27. The computer-implemented method of claim 26, wherein providing the user interface for generating constraints further comprises:
describing resource constraints in a natural language; and
allowing for modification of resource constraint clauses expressed in the natural language.

28. The computer-implemented method of claim 26, wherein generating the resource schedule further comprises:
assigning resources to slots;
propagating constraints; and
backtracking as necessary.

29. The computer-implemented method of claim 26, wherein generating the schedule further comprises:
generating a list of slots; and
assigning the resources to appropriate slots in the list of the slots.

30. The computer-implemented method of claim 26, wherein modifying the resource constraints by: (i) replacing each doubly negated clause with a logically equivalent positive clause, and (ii) adding to the set of resource constraints one or more logically equivalent contrapositive constraints for each conditional constraint.

31. A non-transitory computer readable medium containing instructions, executed in a processor, for performing the steps of:
storing, in a memory structured to enable accessing stored scheduling parameters for optimized scheduling of resources, the scheduling parameters including: (i) a set of resources, each resource having any number of associated user-defined attributes, (ii) at least one calendar having a user-defined plurality of temporal intervals representing a pattern of user-specified dates, for utilizing resources in the set, (iii) at least one shift, each shift including a user defined pattern of time periods representing a recurring pattern of time periods for resource utilization, (iv) at least one slot representing resource demand, resource demand being demand for one or more individual resources of the set of resources during at least one user selected shift of the at least one shifts, and (v) a set of natural language resource constraints of the resources in the set based on the at least one calendar and the at least one slot, the natural language resource constraints generated by the user;

creating a calendar for resource scheduling based on the at least one calendar in memory;

selecting a shift from the at least one shift in memory, wherein allocating the selected shift to a time interval of the created calendar, the shift comprising slots representing resource demand for the time interval of the created calendar; and generating a schedule by assigning resources from the set of resources in the memory to the shift slots by accessing the memory to apply the set of natural language resource constraints to: (i) attributes of each resource of the set of resources and (ii) attributes of the shift, to determine the resources that optimally fulfill the respective resource demands of each shift slot, the applying of the set of natural language resource constraints include:

(a) eliminating the natural language resource constraints that have no effect on the assigning and assigning resources to the shift slots based on remaining natural language resource constraints, and (b) automatically modifying the remaining natural language resource constraints based on attributes of the set of resources and attributes of the shift, such that applying the modified resource constraints optimize the assigning of the resources to the shift slots;

wherein generating the schedule:

schedules simultaneously multiple resources of the set of the resources, such that the simultaneously scheduled multiple resources satisfy demands for resources represented by the shift slots; and presenting a graphical user interface as a display and enabling the user to define at least one attribute of the stored scheduling parameters with objects, including employees, resources, calendars, shift slots, assignments, and replacements by presenting a range of choices for type of each attribute, the choices being at least one of a defined list of alpha-numeric strings, numeric values having defined numerical limits, or a Boolean operator, and to generate the natural language resource constraints.

32. The computer readable medium of claim 31, wherein modifying the resource constraints by: (i) replacing each doubly negated clause with a logically equivalent positive clause, and (ii) adding to the set of resource constraints one or more logically equivalent contrapositive constraints for each conditional constraint.

\* \* \* \* \*